(12) United States Patent
Crowl et al.

(10) Patent No.: US 7,094,890 B1
(45) Date of Patent: Aug. 22, 2006

(54) ARTHRITIS-ASSOCIATED PROTEIN

(75) Inventors: Robert Mitchell Crowl, Berkeley Heights, NJ (US); Daniel C. Luk, Passaic, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/522,699

(22) Filed: Mar. 10, 2000

(51) Int. Cl.
*C07H 21/04* (2006.01)

(52) U.S. Cl. .................. 536/23.5; 435/69.1; 435/325

(58) Field of Classification Search .............. 536/23.5; 435/69.1, 325
See application file for complete search history.

(56) References Cited

PUBLICATIONS

Vollhardt. Organic Chemistry WH Freeman and Co. NY Publishers, 1987, p. 1261.*
Muzny et al., Genbank accession No. AC004616, Apr. 15, 1998.*
Genbank submission Accession No. AC004616, 1998.
Genbank submission Accession No. CAB43220, 1999.

* cited by examiner

*Primary Examiner*—Patrick J. Nolan
(74) *Attorney, Agent, or Firm*—David E. Wildman

(57) ABSTRACT

Disclosed are methods and compositions for early diagnosis, monitoring and treatment of cartilage degenerative conditions, including forms of arthritis. In particular, the invention relates to a protein, termed "adlican," that is differentially transcribed and expressed in human subjects suffering from arthritis, such as osteoarthritis (OA) and rheumatoid arthritis (RA) compared with non-arthritis sufferers, antibodies which recognize this protein, and methods for diagnosing arthritis.

10 Claims, 5 Drawing Sheets

```
ATGCCCAAGCGCGCGCACTGGGGGGCCCTCTCCGTGGTGCTGATCCTGCTTTGGGGCCATCCGCGAGTGGCGCTGGCCTGCCCGCATCCTTGTGCCT
GCTACGTCCCCAGCGAGGTCCACTGCACGTTCCGATCCCTGGCTTCCGTGCCCGCTGGCATTGCTAGACACGTGGAAAGAATCAATTTGGGGTTTAA
TAGCATACAGGCCCTGTCAGAAACCTCATTTGCAGGACTGACCAAGTTGGAGCTACTTATGATTCACGGCAATGAGATCCCAAGCATCCCCGATGGA
GCTTTAAGAGACCTCAGCTCTCTTCAGGTTTTCAAGTTCAGCTACAACAAGCTGAGAGTGATCACAGGACAGACCCTCCAGGGTCTCTCTAACTTAA
TGAGGCTGCACATTGACCACAACAAGATCGAGTTTATCCACCCTCAAGCTTTCAACGGCTTAACGTCTCTGAGGCTACTCCATTTGGAAGGAAATCT
CCTCCACCAGCTGCACCCCAGCACCTTCTCCACGTTCACATTTTTGGATTATTTCAGACTCTCCACCATAAGGCACCTCTACTTAGCAGAGAACATG
GTTAGAACTCTTCCTGCCAGCATGCTTCGGAACATGCCGCTTCTGGAGAATCTTTACTTGCAGGGAAATCCGTGGACCTGCGATTGTGAGATGAGAT
GGTTTTTGGAATGGGATGCAAAATCCAGAGGAATTCTGAAGTGTAAAAAGGACAAAGCTTATGAAGGCGGTCAGTTGTGTGCAATGTGCTTCAGTCC
AAAGAAGTTGTACAAACATGAGATACACAAGCTGAAGGACATGACTTGTCTGAAGCCTTCAATAGAGTCCCCTCTGAGACAGAACAGGAGCAGGAGT
ATTGAGGAGGAGCAAGAACAGGAAGAGGATGGTGGCAGCCAGCTCATCCTGGAGAAATTCCAACTGCCCCAGTGGAGCATCTCTTTGAATATGACCG
ACGAGCACGGGAACATGGTGAACTTGGTCTGTGACATCAAGAAACCAATGGATGTGTACAAGATTCACTTGAACCAAACGGATCCTCCAGATATTGA
CATAAATGCAACAGTTGCCTTGGACTTTGAGTGTCCAATGACCCGAGAAAACTATGAAAAGCTATGAAAATTGATAGCATACTACAGTGAAGTTCCC
GTGAAGCTACACAGAGAGCTCATGCTCAGCAAAGACCCCAGAGTCAGCTACCAGTACAGGCAGGATGCTGATGAGGAAGCTCTTTACTACACAGGTG
TGAGAGCCCAGATTCTTGCAGAACCAGAATGGGTCATGCAGCCATCCATAGATATCCAGCTGAACCGACGTCAGAGTACGGCCAAGAAGGTGCTACT
TTCCTACTACACCCAGTATTCTCAAACAATATCCACCAAAGATACAAGGCAGGCTCGGGGCAGAAGCTGGGTAATGATTGAGCCTAGTGGAGCTGTG
CAAAGAGATCAGACTGTCCTGGAAGGGGGTCCATGCCAGTTGAGCTGCAACGTGAAAGCTTCTGAGAGTCCATCTATCTTCTGGGTGCTTCCAGATG
GCTCCATCCTGAAAGCGCCCATGGATGACCCAGACAGCAAGTTCTCCATTCTCAGCAGTGGCTGGCTGAGGATCAAGTCCATGGAGCCATCTGACTC
AGGCTTGTACCAGTGCATTGCTCAAGTGAGGGATGAAATGGACCGCATGGTATATAGGGTACTTGTGCAGTCTCCCTCCACTCAGCCAGCCGAGAAA
GACACAGTGACAATTGGCAAGAACCCAGGGGAGTCGGTGACATTGCCTTGCAATGCTTTAGCAATACCCGAAGCCCACCTTAGCTGGATTCTTCCAA
ACAGAAGGATAATTAATGATTTGGCTAACACATCACATGTATACATGTTGCCAAATGGAACTCTTTCCATCCCAAAGGTCCAAGTCAGTGATAGTGG
TTACTACAGATGTGTGGCTGTCAACCAGCAAGGGGCAGACCATTTTACGGTGGGAATCACAGTGACCAAGAAAGGGTCTGGCTTGCCATCCAAAAGA
GGCAGACGCCCAGGTGCAAAGGCTCTTTCCAGAGTCAGAGAAGACATCGTGGAGGATGAAGGGGGCTCGGGCATGGGAGATGAAGAGAACACTTCAA
GGAGACTTCTGCATCCAAAGGACCAAGAGGTGTTCCTCAAAACAAAGGATGATGCCATCAATGGAGACAAGAAAGCCAAGAAAGGGAGAAGAAAGCT
GAAACTCTGGAAGCATTCGGAAAAAAGAACCAGAGACCAATGTTGCAGAAGGTCGCAGAGTGTTTGAATCTAGACGAAGGATAAACATGGCAAACAAA
CAGATTAATCCGGAGCGCTGGGCTGATATTTTAGCCAAAGTCCGTGGGAAAAATCTCCCTAAGGGCACAGAAGTACCCCCGTTGATTAAAACCACAA
GTCCTCCATCCTTGAGCCTAGAAGTCACACCACCTTTTCCTGCTGTTTCTCCCCCCTCAGCATCTCCTGTGCAGACAGTAACCAGTGCTGAAGAATC
CTCAGCAGATGTACCTCTACTTGGTGAAGAAGAGCACGTTTTGGGTACCATTTCCTCAGCCAGCATGGGGCTAGAACACAACCACAATGGAGTTATT
CTTGTTGAACCTGAAGTAACAAGCACACCTCTGGAGGAAGTTGTTGATGACCTTTCTGAGAAGACTGAGGAGATAACTTCCACTGAAGGAGACCTGA
AGGGGACAGCAGCCCCTACACTTATATCTGAGCCTTATGAACCATCTCCTACTCTGCACACATTAGACACAGTCTATGAAAAGCCCACCCATGAAGA
GACGGCAACAGAGGGTTGGTCTGCAGCAGATGTTGGATCGTCACCAGAGCCCACATCCAGTGAGTATGAGCCTCCATTGGATGCTGTCTCCTTGGCT
GAGTCTGAGCCCATGCAATACTTTGACCCAGATTTGGAGACTAAGTCACAACCAGATGAGGATAAGATGAAAGAAGACACCTTTGCACACCTTACTC
CAACCCCCACCATCTGGGTTAATGACTCCAGTACATCACAGTTATTTGAGGATTCTACTATAGGGGAACCAGGTGTCCCAGGCCAATCACATCTACA
AGGACTGACAGACAACATCCACCTTGTGAAAAGTAGTCTAAGCACTCAAGACACCTTACTGATTAAAAAGGGTATGAAAGAGATGTCTCAGACACTA
CAGGGAGGAAATATGCTAGAGGGAGACCCCACACACTCCAGAAGTTCTGAGAGTGAGGGCCAAGAGAGCAAATCCATCACTTTGCCTGACTCCACAC
TGGGTATAATGAGCAGTATGTCTCCAGTTAAGAAGCCTGCGGAAACCACAGTTGGTACCCTCCTAGACAAAGCACCCAACAGTAACAACAACACC
AAGGCAAAAAGTTGCTCCGTCATCCACCATGAGCACTCACCCTTCTCGAAGGAGACCCAACGGGAGAAGGAGATTACGCCCAACAAATTCCGCCAC
CGGCACAAGCAAACCCCACCCACAACTTTTGCCCCATCAGAGACTTTTTCTACTCAACCAACTCAAGCACCTGACATTAAGATTTCAAGTCAAGTGG
AGAGTTCTCTGGTTCCTACAGCTTGGGTGGATAACACAGTTAATACCCCCAAACAGTTGGAAATGGAGAAGAATGCAGAACCCACATCCAAGGGAAC
ACCACGGAGAAAACACGGGAAGAGGCCAAACAAACATCGATATACCCCTTCTACAGTGAGCTCAAGAGCGTCCGGATCAAGCCCAGCCCTTCTCCA
GAAAATAAACATAGAAACATTGTTACTCCCAGTTCAGAAACTATACTTTTGCCTAGAACTGTTTCTCTGAAAACTGAGGGCCCTTATGATTCCTTAG
ATTACATGACAACCACCAGAAAAATATATTCATCTTACCCTAAAGTCCAAGAGACACTTCCAGTCACATATAAACCCACATCAGATGGAAAAGAAAT
TAAGGATGATGTTGCCACAAATGTTGACAAACATAAAAGTGACATTTTAGTCACTGGTGAATCAATTACTAATGCCATACCAATCCAACTTCTCGCTCCTTG
GTCTCCACTATGGGAGAATTTAAGGAAGAATCCTCTCCTGTAGGCTTTCCAGGAACTCCAACCTGGAATCCCTCAAGGACGGCCCAGCCTGGGAGGC
TACAGACAGACATACCTGTTACCACTTCTGGGGAAAATCTTACAGACCCTCCCCTTCTTAAAGAGCTTGAGGATGTGGATTTCACTTCCGAGTTTTT
GTCCTCTTTGACAGTCTCCACACCATTTCACCAGGAAGGAGGTGGTTCTTCCACAACTCTCTCAAGCATAAAAGTGGAGGTGGCTTCAAGTCAGGCA
GAAACCACCACCCCTTGATCAAGATCATCTTGAAACCACTGTGGCTATTCTCCTTTCTGAAACATAGACCACAGAATCACACCCCTACTGCTGCCCGGA
TGAAGGAGCCAGCATCCTCGTCCCCATCCACAATTCTCATGTCTTTGGGACAAAACCACCACCACTAAGCAGCACTTCCCAGTCCAAGAATATCTCA
AGCATCTAGAGATTCCAAGGAAAATGTTTTCTTGAATTATGTGGGGAATCCAGAAACAGAAGCAACCCCAGTCAACAATGAAGGAACACAGCATATG
TCAGGGCCAAATGAATTATCAACACCCTCTTCCGACCGGGATGCATTTAACTTGTCTACAAAGCTGGAAATTGGAAAAGCAAGTATTTGGTAGTAGGA
GTCTACCACGTGGCCCAGATAGCCAACGCCAGGATGGAAGAGTTCATGCTTCTCATCAACTAACCAGAGTCCCTGCCAAACCCATCCTACCAACAGC
AACAGTGAGGCTACCTGAAATGTCCACACAAAGCGCTTCCAGATACTTTGTAACTTCCCAGTCACCTCGTCACTGGACCAACAAACCGGAAATAACT
ACATATCCTTCGGGGCTTTGCCAGAGAACAAACAGTTTACAACTCCAAGATTATCAAGTACAACAATTCCTCTCCCATTGCACATGTCCAAACCCA
GCATTCCTAGTAAGTTTACTGACCGAAGAACTGACCAATTCAATGGTTACTCCAAAGTGTTTGGAAATAACAACATCCCTGAGGCAAGAAACCCAGT
TGGAAAGCCTCCCAGTCCAAGAATTCCTCATTATTCCAATGGAAGACTCCCCTTTCTTTACCAACAAGACTCTTTCTTTTCCACAGTTGGGAGTCACC
CGGAGACCCCAGATACCCACTTCTCCTGCCCCAGTAATGAGAGAGAGAAAGTTATTCCAGGTTCCTACAACAGGATACATTCCCATAGCACCTTCC
ATCTGGACTTTGGCCCTCCGGCACCTCCGTTGTTGCACACTCCGCAGACCACGGGATCACCCTCAACTAACTTACAGAATATCCCTATGGTCTCTTC
CACCCAGAGTTCTATCTCCTTTATAACATCTTCTGTCCAGTCCTCAGGGAAGCTTCCACCAGAGCAGCTCAAAGTTCTTTGCAGGAGGACCTCCTGCA
TCCAAATTCTGGTCTCTTGGGGAAAAGCCCCAAATCCTCACCAAGTCCCCACAGACTGTGTTCCGTCACCGCTGAGACAGACACTGTGTTCCCCTGTG
AGGCAACAGGAAAACAAAGCCTTTCGTTACTTGGACAAAGGTTTCCACAGGAGCTCTTATGACTCCGAATACCAGGATACAACGGTTTGAGGTTCT
CAAGAACGGTACCTTAGTGATACGGAAGGTTCAAGTACAAGATCGAGGCCAGTATATGTGCACCGCCAGCAACCTGCACGGCCTGGACAGGATGGTG
GTCTTGCTTTCGGTCACCGTGCAGCAACCTCAAATCCTAGCCTCCCACTACCAGGACGTCACTGTCTACCTGGGAGACACCATTGCAATGGAGTGTC
TGGCCAAAGGGACCCCAGCCCCCCAAATTTCCTGGATCTTCCCTGACAGGAGGGTGTGGCAAACTGTGTCCCCCGTGGAGAGCCGCATCACCCTGCA
CGAAAACCGGACCCTTTCCATCAAGGAGGCGTCCTTCTCAGACAGAGGCGTCTATAAGTGCGTGGCCAGCAATGCAGCCGGGGCGGACAGCCTGGCC
ATCCGCCTGCACGTGGCGGCACTGCCCCCCGTTATCCACCAGGAGAAGCTGGAGAACATCTCGCTGCCCCCGGGGCTCAGCATTCACATTCACTGCA
CTGCCAAGGCTGCGCCCCTGCCCAGCGTGCGCTGGGTGCTCGGGGACGGTACCCAGATCCGCCCCTCGCAGTTCCTCCACGGGAACTTGTTTGTTTT
CCCCAACGGGACGCTCTACATCCGCAACCTCGCGCCCAAGGACAGCGGGCGCTATGAGTGCGTGGCCGCCAACCTGGTAGGCTCCGCGCGCAGGACG
GTGCAGCTGAACGTGCAGCGTGCAGCAGCCAACGCGCGCATCACGGGCACCTCCCCGCGGAGGACGGACGTCAGGTACGGAGGAACCCTCAAGCTGG
```

FIG. 1

```
ACTGCAGCGCCTCGGGGGACCCCTGGCCGCGCATCCTCTGGAGGCTGCCGTCCAAGAGGATGATCGACGCGCTCTTCAGTTTTGATAGCAGAATCAA
GGTGTTTGCCAATGGGACCCTGGTGGTGAAATCAGTGACGGACAAAGATGCCGGAGATTACCTGTGCGTAGCTCGAAATAAGGTTGGTGATGACTAC
GTGGTGCTCAAAGTGGATGTGGTGATGAAACCGGCCAAGATTGAACACAAGGAGGAGAACGACCACAAAGTCTTCTACGGGGGTGACCTGAAAGTGG
ACTGTGTGGCCACCGGGCTTCCCAATCCCGAGATCTCCTGGAGCCTCCCAGACGGGAGTCTGGTGAACTCCTTCATGCAGTCGGATGACAGCGGTGG
ACGCACCAAGCGCTATGTCGTCTTCAACAATGGGACACTCTACTTTAACGAAGTGGGGATGAGGGAGGAAGGAGACTACACCTGCTTTGCTGAAAAT
CAGGTCGGGAAGGACGAGATGAGAGTCAGAGTCAAGGTGGTGACAGCGCCCGCCACCATCCGGAACAAGACTTACTTGGCGGTTCAGGTGCCCTATG
GAGACGTGGTCACTGTAGCCTGTGAGGCCAAAGGAGAACCCATGCCCAAGGTGACTTGGTTGTCCCCAACCAACAAGGTGATCCCCACCTCCTCTGA
GAAGTATCAGATATACCAAGATGGCACTCTCCTTATTCAGAAAGCCCAGCGTTCTGACAGCGGCAACTACACCTGCCTGGTCAGGAACAGCGCGGGA
GAGGATAGGAAGACGGTGTGGATTCACGTCAACGTCCAGCCACCCAAGATCAACGGTAACCCCAACCCCATCACCACCGTGCGGGAGATAGCAGCCG
GGGGCAGTCGGAAACTGATTGACTGCAAAGCTGAAGGCATCCCCACCCCGAGGGTGTTATGGGCTTTTCCCGAGGGTGTGGTTCTGCCAGCTCCATA
CTATGGAAACCGGATCACTGTCCATGGCAACGGTTCCCTGGACATCAGGAGTTTGAGGAAGAGCGACTCCGTCCAGCTGGTATGCATGGCACGCAAC
GAGGGAGGGGAGGCGAGGTTGATCGTGCAGCTCACTGTCCTGGAGCCCATGGAGAAACCCATCTTCCACGACCCGATCAGCGAGAAGATCACGGCCA
TGGCCGGGCCACACCATCAGCCTCAACTGCTCTGCCGCGGGGACCCCGACACCCAGCCTGGTGTGGGTCCTTCCCAATGGCACCGATCTGCAGAGTGG
ACAGCAGCTGCAGCGCTTCTACCACAAGGCTGACGGCATGCTACACATTAGCGGTCTCTCCTCGGTGGACGCTGGGGCCTACCGCTGCGTGGCCCGC
AATGCCGCTGGCCACACGGGAGAGGCTGGTCTCCCTGAAGGTGGGACTGAAGCCAGAAGCAAACAAGCAGTATCATAACCTGGTCAGCATCATCAATG
GTGAGACCCTGAAGCTCCCCTGCACCCCTCCCGGGGCTGGGCAGGGACGTTTCTCCTGGACGCTCCCCAATGGCATGCATCTGGAGGGCCCCCAAAC
CCTGGGACGCGTTTCTCTTCTGGACAATGGCACCCTCACGGTTCGTGAGGCCTCGGTGTTTGACAGGGGTACCTATGTATGCAGGATGGAGACGGAG
TACGGCCCTTCGGTCACCAGCATCCCCGTGATTGTGATCGCCTATCCTCCCGGATCACCGAGCCCACCCCGGTCATCTACACCCGGCCCGGGA
ACACCGTGAAACTGAACTGCATGGCTATGGGGATTCCCAAAGCTGACATCACGTGGGAGTTACCGGATAAGTCGCATCTCGAAGGCAGGGGTTCAGGC
TCGTCTGTATGGAAACAGATTTCTTCACCCCCAGGGATCACTGACCATCCAGCATGCCACACAGAGAGATGCCGGCTTCTACAAGTGCATGGCAAAA
AACATTCTCGGCAGTGACTCCAAAACAACTTACATCCACGTCTTCTGAAATGTGGATTCCAGAATGATTGCTTAGGAACTGACAACAAAGCGGGGTT
TGTAAGGGAAGCCAGGTTGGGGAATAGGAGCTCTTAAATAATGTGTCACAGTGCATGGTGGCCTCTGGTGGGTTTCAAGTTGAGGTTGATCTTGATC
TACAATTGTTGGGAAAAGGAAGCAATGCAGACACGAGAAGGAGGGCTCAGCCTTGCTGAGACACTTTCTTTTGTGTTTACATCATGCCAGGGGCTTC
ATTCAGGGTGTCTCTGTGCTCTGACTGCAATTTTTCTTCTTTTGCAAATGCCACTCGACTGCCTTCATAAGCGTCCATAGGATATCTGAGGAACATTCA
TCAAAAATAAGCCATAGACATGAACAACACCTCACTACCCCATTGAAGACGCATCACCTAGTTAACCTGCTGCAGTTTTTACATGATAGACTTTGTT
CCAGATTGACAAGTCATCTTTCAGTTATTTCCTCTGTCACTTCAAAACTCCACTTGCCCAATAAGGATTTAGAACCAGAGTGACTGATATATATAT
ATATATTTTAATTCAGAGTTACATACATACAGCTACCATTTTATATGAAAAAAGAAAAACATTTCTTCCTGGAACTCACTTTTTATATAATGTTTTA
TATATATATTTTTTCCTTTCAAATCAGACGATGAGACTAGAAGGAGAAATACTTTCTGTCTTATTAAAATTAATAAATTATTGGTCTTTACAAGACT
TGGATACATTACAGCAGACATGGAAATTAATTTTAAAAAATTTCTCTCCAACCTCCTTCAAATTCAGTCACCACTGTTATATTACCTTCTCCAGGA
ACCCTCCAGTGGGGAAGGCTGCGATATTAGATTTCCTTGTATGCAAAGTTTTTGTTGAAAGCTGTGCTCAGAGGAGGTGAGAGGGAGGAAGGAGAA
AACTGCATCATAACTTTACAGAATTGAATCTAGAGTCTTCCCCGAAAAGCCCAGAAACTTCTCTGCAGTATCTGGCTTGTCCATCTGGTCTAAGGTG
GCTGCTTCTTCCCCAGCCATGAGTCAGTTTGTGCCCATGAATAATACACGACCTGTTATTTCCATGACTGCTTTACTGTATTTTTAAGGTCAATATA
CTGTACATTTGATAATAAAATAATATTCTCCCAAAAAAAAAA
```

FIG. 1 - CONTINUED

```
MPKRAHWGALSVVLILLWGHPRVALACPHPCACYVPSEVHCTFRSLASVPAGIARHVERINLGFNSIQALSETSFAGLTKLELLMIHGNEIPSIPDG
ALRDLSSLQVFKFSYNKLRVITGQTLQGLSNLMRLHIDHNKIEFIHPQAFNGLTSLRLLHLEGNLLHQLHPSTFSTFTFLDYFRLSTIRHLYLAENM
VRTLPASMLRNMPLLENLYLQGNPWTCDCEMRWFLEWDAKSRGILKCKKDKAYEGGQLCAMCFSPKKLYKHEIHKLKDMTCLKPSIESPLRQNRSRS
IEEEQEQEEDGGSQLILEKFQLPQWSISLNMTDEHGNMVNLVCDIKKPMDVYKIHLNQTDPPDIDINATVALDFECPMTRENYEKLWKLIAYYSEVP
VKLHRELMLSKDPRVSYQYRQDADEEALYYTGVRAQILAEPEWVMQPSIDIQLNRRQSTAKKVLLSYYTQYSQTISTKDTRQARGRSWVMIEPSGAV
QRDQTVLEGGPCQLSCNVKASESPSIFWVLPDGSILKAPMDDPDSKFSILSSGWLRIKSMEPSDSGLYQCIAQVRDEMDRMVYRVLVQSPSTQPAEK
DTVTIGKNPGESVTLPCNALAIPEAHLSWILPNRRIINDLANTSHVYMLPNGTLSIPKVQVSDSGYYRCVAVNQQGADHFTVGITVTKKGSGLPSKR
GRRPGAKALSRVREDIVEDEGGSGMGDEENTSRRLLHPKDQEVFLKTKDDAINGDKKAKKGRRKLKLWKHSEKEPETNVAEGRRVFESRRRINMANK
QINPERWADILAKVRGKNLPKGTEVPPLIKTTSPPSLSLEVTPPFPAVSPPSASPVQTVTSAEESSADVPLLGEEEHVLGTISSASMGLEHNHNGVI
LVEPEVTSTPLEEVVDDLSEKTEEITSTEGDLKGTAAPTLISEPYEPSPTLHTLDTVYEKPTHEETATEGWSAADVGSSPEPTSSEYEPPLDAVSLA
ESEPMQYFDPDLETKSQPDEDKMKEDTFAHLTPTPTIWVNDSSTSQLFEDSTIGEPGVPGQSHLQGLTDNIHLVKSSLSTQDTLLIKKGMKEMSQTL
QGGNMLEGDPTHSRSSESEGGQESKSITLPDSTLGIMSSMSPVKKPAETTVGTLLDKDTTTVTTTPRQKVAPSSTMSTHPSRRRPNGRRRLRPNKFRH
RHKQTPPTTFAPSETFSTQPTQAPDIKISSQVESSLVPTAWVDNTVNTPKQLEMEKNAEPTSKGTPRRKHGKRPNKHRYTPSTVSSRASGSKPSPSP
ENKHRNIVTPSSETILLPRTVSLKTEGPYDSLDYMTTTRKIYSSYPKVQETLPVTYKPTSDGKEIKDDVATNVDKHKSDILVTGESITNAIPTSRSL
VSTMGEFKEESSPVGFPGTPTWNPSRTAQPGRLQTDIPVTTSGENLTDPPLLKELEDVDFTSEFLSSLTVSTPFHQEEAGSSTTLSSIKVEVASSQA
ETTTLDQDHLETTVAILLSETRPQNHTPTAARMKEPASSSPSTILMSLGQTTTTKPALPSPRISQASRDSKENVFLNYVGNPETEATPVNNEGTQHM
SGPNELSTPSSDRDAFNLSTKLELEKQVFGSRSLPRGPDSQRQDGRVHASHQLTRVPAKPILPTATVRLPEMSTQSASRYFVTSQSPRHWTNKPEIT
TYPSGALPENKQFTTPRLSSTTIPLPLHMSKPSIPSKFTDRRTDQFNGYSKVFGNNNIPEARNPVGKPPSPRIPHYSNGRLPFFTNKTLSFPQLGVT
RRPQIPTSPAPVMRERKVIPGSYNRIHSHSTFHLDFGPPAPPLLHTPQTTGSPSTNLQNIPMVSSTQSSISFITSSVQSSGSFHQSSSKFFAGGPPA
SKFWSLGEKPQILTKSPQTVSVTAETDTVFPCEATGKPKPFVTWTKVSTGALMTPNTRIQRFEVLKNGTLVIRKVQVQDRGQYMCTASNLHGLDRMV
VLLSVTVQQPQILASHYQDVTVYLGDTIAMECLAKGTPAPQISWIFPDRRVWQTVSPVESRITLHENRTLSIKEASFSDRGVYKCVASNAAGADSLA
IRLHVAALPPVIHQEKLENISLPPGLSIHIHCTAKAAPLPSVRWVLGDGTQIRPSQFLHGNLFVFPNGTLYIRNLAPKDSGRYECVAANLVGSARRT
VQLNVQRAAANARITGTSPRRTDVRYGGTLKLDCSASGDPWPRILWRLPSKRMIDALFSFDSRIKVFANGTLVVKSVTDKDAGDYLCVARNKVGDDY
VVLKVDVVMKPAKIEHKEENDHKVFYGGDLKVDCVATGLPNPEISWSLPDGSLVNSFMQSDDSGGRTKRYVVFNNGTLYFNEVGMREEGDYTCFAEN
QVGKDEMRVRVKVVTAPATIRNKTYLAVQVPYGDVVTVACEAKGEPMPKVTWLSPTNKVIPTSSEKYQIYQDGTLLIQKAQRSDSGNYTCLVRNSAG
EDRKTVWIHVNVQPPKINGNPNPITTVREIAAGGSRKLIDCKAEGIPTPRVLWAFPEGVVLPAPYYGNRITVHGNGSLDIRSLRKSDSVQLVCMARN
EGGEARLIVQLTVLEPMEKPIFHDPISEKITAMAGHTISLNCSAAGTPTPSLVWVLPNGTDLQSGQQLQRFYHKADGMLHISGLSSVDAGAYRCVAR
NAAGHTERLVSLKVGLKPEANKQYHNLVSIINGETLKLPCTPPGAGQGRFSWTLPNGMHLEGPQTLGRVSLLDNGTLTVREASVFDRGTYVCRMETE
YGPSVTSIPIVIAYPPRITSEPTPVIYTRPGNTVKLNCMAMGIPKADITWELPDKSHLKAGVQARLYGNRFLHPQGSLTIQHATQRDAGFYKCMAK
NILGSDSKTTYIHVF
```

FIG. 2

Levels of Adlican mRNA in human cartilage by RT-PCR

SEQUENCE LISTING

<160> NUMBER OF SEQ ID NOS: 9

<210> SEQ ID NO 1
<211> LENGTH: 9645
<212> TYPE: DNA
<213> ORGANISM: Human

<400> SEQUENCE: 1

```
atgcccaagc gcgcgcactg gggggccctc tccgtggtgc tgatcctgct ttggggccat      60
ccgcgagtgg cgctggcctg cccgcatcct tgtgcctgct acgtccccag cgaggtccac     120
tgcacgttcc gatccctggc ttccgtgccc gctggcattg ctagacacgt ggaaagaatc     180
aatttggggt ttaatagcat acaggccctg tcagaaacct catttgcagg actgaccaag     240
ttggagctac ttatgattca cggcaatgag atcccaagca tccccgatgg agctttaaga     300
gacctcagct ctcttcaggt tttcaagttc agctacaaca agctgagagt gatcacagga     360
cagaccctcc agggtctctc taacttaatg aggctgcaca ttgaccacaa caagatcgag     420
tttatccacc ctcaagcttt caacggctta acgtctctga ggctactcca tttggaagga     480
aatctcctcc accagctgca cccagcacc ttctccacgt tcacattttt ggattatttc      540
```

-continued

```
agactctcca ccataaggca cctctactta gcagagaaca tggttagaac tcttcctgcc      600
agcatgcttc ggaacatgcc gcttctggag aatctttact tgcagggaaa tccgtggacc      660
tgcgattgtg agatgagatg gttttttggaa tgggatgcaa aatccagagg aattctgaag     720
tgtaaaaagg acaaagctta tgaaggcggt cagttgtgtg caatgtgctt cagtccaaag      780
aagttgtaca acatgagat acacaagctg aaggacatga cttgtctgaa gccttcaata      840
gagtcccctc tgagacagaa caggagcagg agtattgagg aggagcaaga acaggaagag      900
gatggtggca gccagctcat cctggagaaa ttccaactgc cccagtggag catctctttg      960
aatatgaccg acgagcacgg gaacatggtg aacttggtct gtgacatcaa gaaccaatg     1020 gatgtgtaca agattcactt gaaccaaacg gatcctccag atattgacat aaatgcaaca     1080
gttgccttgg actttgagtg tccaatgacc cgagaaaact atgaaaagct atggaaattg     1140
atagcatact acagtgaagt tcccgtgaag ctacacagag agctcatgct cagcaaagac     1200
cccagagtca gctaccagta caggcaggat gctgatgagg aagctcttta ctacacaggt     1260
gtgagagccc agattcttgc agaaccagaa tgggtcatgc agccatccat agatatccag     1320
ctgaaccgac gtcagagtac ggccaagaag gtgctacttt cctactacac ccagtattct     1380
caaacaatat ccaccaaaga tacaaggcag gctcgggca gaagctgggt aatgattgag     1440
cctagtggga ctgtgcaaag agatcagact gtcctggaag ggggtccatg ccagttgagc     1500
tgcaacgtga agcttctga gagtccatct atcttctggg tgcttccaga tggctccatc     1560
ctgaaagcgc ccatggatga cccagacagc aagttctcca ttctcagcag tggctggctg     1620
aggatcaagt ccatggagcc atctgactca ggcttgtacc agtgcattgc tcaagtgagg     1680
gatgaaatgg accgcatggt atatagggta cttgtgcagt ctccctccac tcagccagcc     1740
gagaaagaca cagtgacaat tggcaagaac ccaggggagt cggtgacatt gccttgcaat     1800
gctttagcaa tacccgaagc ccaccttagc tggattcttc caaacagaag gataattaat     1860
gatttggcta acacatcaca tgtatacatg ttgccaaatg gaactctttc catcccaaag     1920
gtccaagtca gtgatagtgg ttactacaga tgtgtggctg tcaaccagca agggcagac     1980 cattttacgg tgggaatcac agtgaccaag aaagggtctg gcttgccatc caaaagaggc     2040
agacgcccag gtgcaaaggc tcttttccaga gtcagagaag acatcgtgga ggatgaaggg     2100
ggctcgggca tgggagatga agagaacact tcaaggagac ttctgcatcc aaaggaccaa     2160
gaggtgttcc tcaaaacaaa ggatgatgcc atcaatggag acaagaaagc caagaagggg     2220
agaagaaagc tgaaactctg gaagcattcg gaaaaagaac cagagaccaa tgttgcagaa     2280
ggtcgcagag tgtttgaatc tagacgaagg ataaacatgg caaacaaaca gattaatccg     2340
gagcgctggg ctgatatttt agccaaagtc cgtgggaaaa atctccctaa gggcacagaa     2400 gtaccccgt tgattaaaac cacaagtcct ccatccttga gcctagaagt cacaccacct     2460
tttcctgctg tttctccccc ctcagcatct cctgtgcaga cagtaaccag tgctgaagaa     2520
tcctcagcag atgtacctct acttggtgaa gaagagcacg tttgggtac catttcctca     2580 gccagcatgg ggctagaaca caaccacaat ggagttattc ttgttgaacc tgaagtaaca     2640
agcacacctc tggaggaagt tgttgatgac cttttctgaga agactgagga gataacttcc     2700
actgaaggag acctgaaggg gacagcagcc cctacactta tatctgagcc ttatgaacca     2760 tctcctacte tgcacacatt agacacagtc tatgaaaagc ccacccatga agagacggca     2820
acagagggtt ggtctgcagc agatgttgga tcgtcaccag agcccacatc cagtgagtat     2880
gagcctccat tggatgctgt ctccttggct gagtctgagc ccatgcaata ctttgaccca     2940
```

```
gatttggaga ctaagtcaca accagatgag gataagatga aagaagacac ctttgcacac    3000
cttactccaa cccccaccat ctgggttaat gactccagta catcacagtt atttgaggat    3060
tctactatag gggaaccagg tgtcccaggc caatcacatc tacaaggact gacagacaac    3120
atccaccttg tgaaaagtag tctaagcact caagacacct tactgattaa aaagggtatg    3180
aaagagatgt ctcagacact acagggagga aatatgctag agggagaccc cacacactcc    3240
agaagttctg agagtgaggg ccaagagagc aaatccatca cttgcctga ctccacactg     3300 ggtataatga gcagtatgtc tccagttaag aagcctgcgg aaaccacagt tggtaccctc    3360
ctagacaaag acaccacaac agtaacaaca acaccaaggc aaaaagttgc tccgtcatcc    3420
accatgagca ctcacccttc tcgaaggaga cccaacggga aaggagatt acgcccaac     3480 aaattccgcc accggcacaa gcaaacccca cccacaactt ttgccccatc agagacttt    3540 tctactcaac caactcaagc acctgacatt aagatttcaa gtcaagtgga gagttctctg    3600
gttcctacag cttgggtgga taacacagtt aataccccca acagttggaa aatggagaag    3660
aatgcagaac ccacatccaa gggaacacca cggagaaaac acgggaagag gccaaacaaa    3720
catcgatata ccccttctac agtgagctca agagcgtccg gatccaagcc cagcccttct    3780
ccagaaaata aacatagaaa cattgttact cccagttcag aaactatact tttgcctaga    3840
actgtttctc tgaaaactga gggcccttat gattccttag attacatgac aaccaccaga    3900
aaaatatatt catcttaccc taaagtccaa gagacacttc cagtcacata taaacccaca    3960
tcagatggaa aagaaattaa ggatgatgtt gccacaaatg ttgacaaaca taaaagtgac    4020
attttagtca ctggtgaatc aattactaat gccataccaa cttctcgctc cttggtctcc    4080 actatggag aatttaagga agaatcctct cctgtaggct ttccaggaac tccaacctgg    4140
aatccctcaa ggacggccca gcctgggagg ctacagacag acatacctgt taccacttct    4200
ggggaaaatc ttcagacccc tccccttctt aaagagcttg aggatgtgga tttcacttcc    4260 gagttttgt cctctttgac agtctccaca ccatttcacc aggaagaagc tggttcttcc     4320
acaactctct caagcataaa agtggaggtg gcttcaagtc aggcagaaac caccacccctt   4380 gatcaagatc atcttgaaac cactgtggct attctccttt ctgaaactag accacagaat    4440 cacacccta ctgctgcccg gatgaaggag ccagcatcct cgtccccatc cacaattctc     4500
atgtctttgg gacaaaccac caccactaag ccagcacttc ccagtccaag aatatctcaa    4560
gcatctagaa attccaagga aaatgttttc ttgaattatg tggggaatcc agaaacagaa    4620
gcaaccccag tcaacaatga aggaacacag catatgtcag ggccaaatga attatcaaca    4680
ccctcttccg accgggatgc atttaacttg tctacaaagc tggaattgga aaagcaagta    4740
tttggtagta ggagtctacc acgtggccca gatagccaac gccaggatgg aagagttcat    4800
gcttctcatc aactaaccag agtccctgcc aaacccatcc taccaacagc aacagtgagg    4860
ctacctgaaa tgtccacaca aagcgcttcc agatactttg taacttccca gtcacctcgt    4920
cactggacca caaaccgga ataactaca tatccttctg gggctttgcc agagaacaaa       4980
cagtttacaa ctccaagatt atcaagtaca acaattcctc tcccattgca catgtccaaa    5040
cccagcattc ctagtaagtt tactgaccga agaactgacc aattcaatgg ttactccaaa    5100
gtgtttggaa ataacaacat ccctgaggca agaaacccag ttgaaagcc tcccagtcca     5160 agaattcctc attattccaa tggaagactc cctttctta ccaacaagac tctttctttt     5220
ccacagttgg gagtcacccg gagacccag atacccactt ctcctgcccc agtaatgaga     5280
```

-continued

```
gagagaaaag ttattccagg ttcctacaac aggatacatt cccatagcac cttccatctg    5340
gactttggcc ctccggcacc tccgttgttg cacactccgc agaccacggg atcaccctca    5400
actaacttac agaatatccc tatggtctct tccacccaga gttctatctc ctttataaca    5460
tcttctgtcc agtcctcagg aagcttccac cagagcagct caaagttctt tgcaggagga    5520
cctcctgcat ccaaattctg gtctcttggg gaaaagcccc aaatcctcac caagtcccca    5580
cagactgtgt ccgtcaccgc tgagacagac actgtgttcc cctgtgaggc aacaggaaaa    5640
ccaaagcctt tcgttacttg gacaaaggtt tccacaggag ctcttatgac tccgaatacc    5700
aggatacaac ggtttgaggt tctcaagaac ggtaccttag tgatacggaa ggttcaagta    5760
caagatcgag gccagtatat gtgcaccgcc agcaacctgc acggcctgga caggatggtg    5820
gtcttgcttt cggtcaccgt gcagcaacct caaatcctag cctcccacta ccaggacgtc    5880
actgtctacc tgggagacac cattgcaatg gagtgtctgg ccaaagggac cccagccccc    5940
caaatttcct ggatcttccc tgacaggagg gtgtggcaaa ctgtgtcccc cgtggagagc    6000
cgcatcaccc tgcacgaaaa ccggacccct tccatcaagg aggcgtcctt ctcagacaga    6060
ggcgtctata agtgcgtggc cagcaatgca gccggggcgg acagcctggc catccgcctg    6120
cacgtggcgg cactgccccc cgttatccac caggagaagc tggagaacat ctcgctgccc    6180
ccggggctca gcattcacat tcactgcact gccaaggctg cgcccctgcc cagcgtgcgc    6240
tgggtgctcg gggacggtac ccagatccgc ccctcgcagt tcctccacgg gaacttgttt    6300
gttttcccca acgggacgct ctacatccgc aacctcgcgc caaggacag cgggcgctat    6360 gagtgcgtgg ccgccaacct ggtaggctcc gcgcgcagga cggtgcagct gaacgtgcag    6420
cgtgcagcag ccaacgcgcg catcacgggc acctcccgc ggaggacgga cgtcaggtac    6480
ggaggaaccc tcaagctgga ctgcagcgcc tcggggacc cctggccgcg catcctctgg    6540
aggctgccgt ccaagaggat gatcgacgcg ctcttcagtt ttgatagcag aatcaaggtg    6600
tttgccaatg ggaccctggt ggtgaaatca gtgacggaca aagatgccgg agattacctg    6660
tgcgtagctc gaaataaggt tggtgatgac tacgtggtgc tcaaagtgga tgtggtgatg    6720
aaaccggcca agattgaaca caaggaggag aacgaccaca aagtcttcta cggggtgac    6780 ctgaaagtgg actgtgtggc caccgggctt cccaatcccg agatctcctg gagcctccca    6840
gacgggagtc tggtgaactc cttcatgcag tcggatgaca gcgtggacg caccaagcgc    6900 tatgtcgtct tcaacaatgg gacactctac tttaacgaag tggggatgag ggaggaagga    6960
gactacacct gctttgctga aaatcaggtc gggaaggacg agatgagagt cagagtcaag    7020
gtggtgacag cgcccgccac catccggaac aagacttact ggcggttca ggtgccctat    7080 ggagacgtgg tcactgtagc ctgtgaggcc aaaggagaac ccatgccaa ggtgacttgg    7140 ttgtccccaa ccaacaaggt gatccccacc tcctctgaga gtatcagat ataccaagat    7200 ggcactctcc ttattcagaa agcccagcgt tctgacagcg gcaactacac ctgcctggtc    7260
aggaacagcg cggagagga taggaagacg gtgtggattc acgtcaacgt ccagccaccc    7320
aagatcaacg gtaaccccaa ccccatcacc accgtgcggg agatagcagc cggggcagt    7380 cggaaactga ttgactgcaa agctgaaggc atccccaccc cgagggtgtt atgggctttt    7440
cccgagggtg tggttctgcc agctccatac tatggaaacc ggatcactgt ccatggcaac    7500
ggttccctgg acatcaggag tttgaggaag agcgactccg tccagctggt atgcatggca    7560
cgcaacgagg aggggaggc gaggttgatc gtgcagctca ctgtcctgga gcccatggag    7620
aaacccatct tccacgaccc gatcagcgag aagatcacgg ccatggcggg ccacaccatc    7680
```

-continued

```
agcctcaact gctctgccgc ggggaccccg acacccagcc tggtgtgggt ccttcccaat    7740
ggcaccgatc tgcagagtgg acagcagctg cagcgcttct accacaaggc tgacggcatg    7800
ctacacatta gcggtctctc ctcggtggac gctggggcct accgctgcgt ggcccgcaat    7860
gccgctggcc acacggagag gctggtctcc ctgaaggtgg actgaagcc agaagcaaac     7920 aagcagtatc ataacctggt cagcatcatc aatggtgaga ccctgaagct cccctgcacc    7980
cctcccgggg ctgggcaggg acgtttctcc tggacgctcc ccaatggcat gcatctggag    8040
ggcccccaaa ccctgggacg cgtttctctt ctggacaatg gcaccctcac ggttcgtgag    8100
gcctcggtgt ttgacagggg tacctatgta tgcaggatgg agacggagta cggcccttcg    8160
gtcaccagca tccccgtgat tgtgatcgcc tatcctcccc ggatcaccag cgagcccacc    8220
ccggtcatct acacccggcc cgggaacacc gtgaaactga actgcatggc tatggggatt    8280
cccaaagctg acatcacgtg ggagttaccg gataagtcgc atctgaaggc aggggttcag    8340
gctcgtctgt atggaaacag atttcttcac ccccagggat cactgaccat ccagcatgcc    8400
acacagagag atgccggctt ctacaagtgc atggcaaaaa acattctcgg cagtgactcc    8460
aaaacaactt acatccacgt cttctgaaat gtggattcca gaatgattgc ttaggaactg    8520
acaacaaagc ggggtttgta agggaagcca ggttggggaa taggagctct taaataatgt    8580
gtcacagtgc atggtggcct ctggtgggtt tcaagttgag gttgatcttg atctacaatt    8640
gttgggaaaa ggaagcaatg cagacacgag aaggagggct cagccttgct gagacacttt    8700
cttttgtgtt tacatcatgc caggggcttc attcagggtg tctgtgctct gactgcaatt    8760
tttcttcttt tgcaaatgcc actcgactgc cttcataagc gtccatagga tatctgagga    8820
acattcatca aaaataagcc atagacatga acaacacctc actacccat tgaagacgca     8880 tcacctagtt aacctgctgc agttttaca tgatagactt tgttccagat tgacaagtca     8940
tctttcagtt atttcctctg tcacttcaaa actccagctt gcccaataag gatttagaac    9000
cagagtgact gatatatata tatataittt aattcagagt tacatacata cagctaccat    9060
tttatatgaa aaaagaaaaa catttcttcc tggaactcac ttttatata atgttttata    9120 tatatatttt ttcctttcaa atcagacgat gagactagaa ggagaatac tttctgtcitt    9180 attaaaatta ataattatt ggtcttaca agacttggat acattacagc agacatggaa     9240
atataatttt aaaaaatttc tctccaacct ccttcaaatt cagtcaccac tgttatatta    9300
ccttctccag gaaccctcca gtggggaagg ctgcgatatt agatttcctt gtatgcaaag    9360
tttttgttga aagctgtgct cagaggaggt gagaggagag gaaggagaaa actgcatcat    9420
aactttacag aattgaatct agagtcttcc ccgaaaagcc cagaaacttc tctgcagtat    9480
ctggcttgtc catctggtct aaggtggctg cttcttcccc agccatgagt cagtttgtgc    9540
ccatgaataa tacacgacct gttatttcca tgactgcttt actgtatttt taaggtcaat    9600
atactgtaca tttgataata aaataatatt ctcccaaaaa aaaaa                    9645
```

<210> SEQ ID NO 2
<211> LENGTH: 2828
<212> TYPE: PRT
<213> ORGANISM: Human

<400> SEQUENCE: 2

Met Pro Lys Arg Ala His Trp Gly Ala Leu Ser Val Val Leu Ile Leu
1               5                   10                  15

Leu Trp Gly His Pro Arg Val Ala Leu Ala Cys Pro His Pro Cys Ala

-continued

```
            20                  25                  30
Cys Tyr Val Pro Ser Glu Val His Cys Thr Phe Arg Ser Leu Ala Ser
        35                  40                  45
Val Pro Ala Gly Ile Ala Arg His Val Glu Arg Ile Asn Leu Gly Phe
    50                  55                  60
Asn Ser Ile Gln Ala Leu Ser Glu Thr Ser Phe Ala Gly Leu Thr Lys
 65                  70                  75                  80
Leu Glu Leu Leu Met Ile His Gly Asn Glu Ile Pro Ser Ile Pro Asp
                85                  90                  95
Gly Ala Leu Arg Asp Leu Ser Ser Leu Gln Val Phe Lys Phe Ser Tyr
            100                 105                 110
Asn Lys Leu Arg Val Ile Thr Gly Gln Thr Leu Gln Gly Leu Ser Asn
        115                 120                 125
Leu Met Arg Leu His Ile Asp His Asn Lys Ile Glu Phe Ile His Pro
130                 135                 140
Gln Ala Phe Asn Gly Leu Thr Ser Leu Arg Leu Leu His Leu Glu Gly
145                 150                 155                 160
Asn Leu Leu His Gln Leu His Pro Ser Thr Phe Ser Thr Phe Thr Phe
                165                 170                 175
Leu Asp Tyr Phe Arg Leu Ser Thr Ile Arg His Leu Tyr Leu Ala Glu
            180                 185                 190
Asn Met Val Arg Thr Leu Pro Ala Ser Met Leu Arg Asn Met Pro Leu
        195                 200                 205
Leu Glu Asn Leu Tyr Leu Gln Gly Asn Pro Trp Thr Cys Asp Cys Glu
210                 215                 220
Met Arg Trp Phe Leu Glu Trp Asp Ala Lys Ser Arg Gly Ile Leu Lys
225                 230                 235                 240
Cys Lys Lys Asp Lys Ala Tyr Glu Gly Gly Gln Leu Cys Ala Met Cys
                245                 250                 255
Phe Ser Pro Lys Lys Leu Tyr Lys His Glu Ile His Lys Leu Lys Asp
            260                 265                 270
Met Thr Cys Leu Lys Pro Ser Ile Glu Ser Pro Leu Arg Gln Asn Arg
        275                 280                 285
Ser Arg Ser Ile Glu Glu Gln Glu Gln Glu Glu Asp Gly Gly Ser
    290                 295                 300
Gln Leu Ile Leu Glu Lys Phe Gln Leu Pro Gln Trp Ser Ile Ser Leu
305                 310                 315                 320
Asn Met Thr Asp Glu His Gly Asn Met Val Asn Leu Val Cys Asp Ile
                325                 330                 335
Lys Lys Pro Met Asp Val Tyr Lys Ile His Leu Asn Gln Thr Asp Pro
            340                 345                 350
Pro Asp Ile Asp Ile Asn Ala Thr Val Ala Leu Asp Phe Glu Cys Pro
        355                 360                 365
Met Thr Arg Glu Asn Tyr Glu Lys Leu Trp Lys Leu Ile Ala Tyr Tyr
    370                 375                 380
Ser Glu Val Pro Val Lys Leu His Arg Glu Leu Met Leu Ser Lys Asp
385                 390                 395                 400
Pro Arg Val Ser Tyr Gln Tyr Arg Gln Asp Ala Asp Glu Glu Ala Leu
                405                 410                 415
Tyr Tyr Thr Gly Val Arg Ala Gln Ile Leu Ala Glu Pro Glu Trp Val
            420                 425                 430
Met Gln Pro Ser Ile Asp Ile Gln Leu Asn Arg Arg Gln Ser Thr Ala
```

-continued

```
                435                 440                 445
Lys Lys Val Leu Leu Ser Tyr Tyr Thr Gln Tyr Ser Gln Thr Ile Ser
    450                 455                 460
Thr Lys Asp Thr Arg Gln Ala Arg Gly Arg Ser Trp Val Met Ile Glu
465                 470                 475                 480
Pro Ser Gly Ala Val Gln Arg Asp Gln Thr Val Leu Glu Gly Gly Pro
                485                 490                 495
Cys Gln Leu Ser Cys Asn Val Lys Ala Ser Glu Ser Pro Ser Ile Phe
                500                 505                 510
Trp Val Leu Pro Asp Gly Ser Ile Leu Lys Ala Pro Met Asp Asp Pro
            515                 520                 525
Asp Ser Lys Phe Ser Ile Leu Ser Ser Gly Trp Leu Arg Ile Lys Ser
        530                 535                 540
Met Glu Pro Ser Asp Ser Gly Leu Tyr Gln Cys Ile Ala Gln Val Arg
545                 550                 555                 560
Asp Glu Met Asp Arg Met Val Tyr Arg Val Leu Val Gln Ser Pro Ser
                565                 570                 575
Thr Gln Pro Ala Glu Lys Asp Thr Val Thr Ile Gly Lys Asn Pro Gly
            580                 585                 590
Glu Ser Val Thr Leu Pro Cys Asn Ala Leu Ala Ile Pro Glu Ala His
        595                 600                 605
Leu Ser Trp Ile Leu Pro Asn Arg Arg Ile Ile Asn Asp Leu Ala Asn
    610                 615                 620
Thr Ser His Val Tyr Met Leu Pro Asn Gly Thr Leu Ser Ile Pro Lys
625                 630                 635                 640
Val Gln Val Ser Asp Ser Gly Tyr Tyr Arg Cys Val Ala Val Asn Gln
                645                 650                 655
Gln Gly Ala Asp His Phe Thr Val Gly Ile Thr Val Thr Lys Lys Gly
            660                 665                 670
Ser Gly Leu Pro Ser Lys Arg Gly Arg Pro Gly Ala Lys Ala Leu
        675                 680                 685
Ser Arg Val Arg Glu Asp Ile Val Glu Asp Glu Gly Ser Gly Met
    690                 695                 700
Gly Asp Glu Glu Asn Thr Ser Arg Arg Leu Leu His Pro Lys Asp Gln
705                 710                 715                 720
Glu Val Phe Leu Lys Thr Lys Asp Asp Ala Ile Asn Gly Asp Lys Lys
                725                 730                 735
Ala Lys Lys Gly Arg Arg Lys Leu Lys Leu Trp Lys His Ser Glu Lys
            740                 745                 750
Glu Pro Glu Thr Asn Val Ala Glu Gly Arg Arg Val Phe Glu Ser Arg
        755                 760                 765
Arg Arg Ile Asn Met Ala Asn Lys Gln Ile Asn Pro Glu Arg Trp Ala
    770                 775                 780
Asp Ile Leu Ala Lys Val Arg Gly Lys Asn Leu Pro Lys Gly Thr Glu
785                 790                 795                 800
Val Pro Pro Leu Ile Lys Thr Thr Ser Pro Pro Ser Leu Ser Leu Glu
                805                 810                 815
Val Thr Pro Pro Phe Pro Ala Val Ser Pro Pro Ser Ala Ser Pro Val
                820                 825                 830
Gln Thr Val Thr Ser Ala Glu Glu Ser Ser Ala Asp Val Pro Leu Leu
            835                 840                 845
Gly Glu Glu Glu His Val Leu Gly Thr Ile Ser Ser Ala Ser Met Gly
        850                 855                 860
```

-continued

```
Leu Glu His Asn His Asn Gly Val Ile Leu Val Glu Pro Val Thr
865                 870                 875                 880

Ser Thr Pro Leu Glu Glu Val Val Asp Asp Leu Ser Glu Lys Thr Glu
                885                 890                 895

Glu Ile Thr Ser Thr Glu Gly Asp Leu Lys Gly Thr Ala Ala Pro Thr
            900                 905                 910

Leu Ile Ser Glu Pro Tyr Glu Pro Ser Pro Thr Leu His Thr Leu Asp
        915                 920                 925

Thr Val Tyr Glu Lys Pro Thr His Glu Glu Thr Ala Thr Glu Gly Trp
    930                 935                 940

Ser Ala Ala Asp Val Gly Ser Ser Pro Glu Pro Thr Ser Ser Glu Tyr
945                 950                 955                 960

Glu Pro Pro Leu Asp Ala Val Ser Leu Ala Glu Ser Glu Pro Met Gln
                965                 970                 975

Tyr Phe Asp Pro Asp Leu Glu Thr Lys Ser Gln Pro Asp Glu Asp Lys
            980                 985                 990

Met Lys Glu Asp Thr Phe Ala His Leu Thr Pro Thr Pro Thr Ile Trp
        995                 1000                1005

Val Asn Asp Ser Ser Thr Ser Gln Leu Phe Glu Asp Ser Thr Ile Gly
    1010                1015                1020

Glu Pro Gly Val Pro Gly Gln Ser His Leu Gln Gly Leu Thr Asp Asn
1025                1030                1035                1040

Ile His Leu Val Lys Ser Ser Leu Ser Thr Gln Asp Thr Leu Leu Ile
                1045                1050                1055

Lys Lys Gly Met Lys Glu Met Ser Gln Thr Leu Gln Gly Gly Asn Met
            1060                1065                1070

Leu Glu Gly Asp Pro Thr His Ser Arg Ser Ser Glu Ser Glu Gly Gln
        1075                1080                1085

Glu Ser Lys Ser Ile Thr Leu Pro Asp Ser Thr Leu Gly Ile Met Ser
    1090                1095                1100

Ser Met Ser Pro Val Lys Lys Pro Ala Glu Thr Thr Val Gly Thr Leu
1105                1110                1115                1120

Leu Asp Lys Asp Thr Thr Thr Val Thr Thr Thr Pro Arg Gln Lys Val
                1125                1130                1135

Ala Pro Ser Ser Thr Met Ser Thr His Pro Ser Arg Arg Arg Pro Asn
            1140                1145                1150

Gly Arg Arg Arg Leu Arg Pro Asn Lys Phe Arg His Arg His Lys Gln
        1155                1160                1165

Thr Pro Pro Thr Thr Phe Ala Pro Ser Glu Thr Phe Ser Thr Gln Pro
    1170                1175                1180

Thr Gln Ala Pro Asp Ile Lys Ile Ser Ser Gln Val Glu Ser Ser Leu
1185                1190                1195                1200

Val Pro Thr Ala Trp Val Asp Asn Thr Val Asn Thr Pro Lys Gln Leu
                1205                1210                1215

Glu Met Glu Lys Asn Ala Glu Pro Thr Ser Lys Gly Thr Pro Arg Arg
            1220                1225                1230

Lys His Gly Lys Arg Pro Asn Lys His Arg Tyr Thr Pro Ser Thr Val
        1235                1240                1245

Ser Ser Arg Ala Ser Gly Ser Lys Pro Ser Pro Ser Pro Glu Asn Lys
    1250                1255                1260

His Arg Asn Ile Val Thr Pro Ser Ser Glu Thr Ile Leu Leu Pro Arg
1265                1270                1275                1280
```

-continued

```
Thr Val Ser Leu Lys Thr Glu Gly Pro Tyr Asp Ser Leu Asp Tyr Met
            1285                1290                1295

Thr Thr Thr Arg Lys Ile Tyr Ser Ser Tyr Pro Lys Val Gln Glu Thr
        1300                1305                1310

Leu Pro Val Thr Tyr Lys Pro Thr Ser Asp Gly Lys Glu Ile Lys Asp
        1315                1320                1325

Asp Val Ala Thr Asn Val Asp Lys His Lys Ser Asp Ile Leu Val Thr
        1330                1335                1340

Gly Glu Ser Ile Thr Asn Ala Ile Pro Thr Ser Arg Ser Leu Val Ser
1345                1350                1355                1360

Thr Met Gly Glu Phe Lys Glu Glu Ser Ser Pro Val Gly Phe Pro Gly
            1365                1370                1375

Thr Pro Thr Trp Asn Pro Ser Arg Thr Ala Gln Pro Gly Arg Leu Gln
            1380                1385                1390

Thr Asp Ile Pro Val Thr Thr Ser Gly Glu Asn Leu Thr Asp Pro Pro
            1395                1400                1405

Leu Leu Lys Glu Leu Glu Asp Val Asp Phe Thr Ser Glu Phe Leu Ser
        1410                1415                1420

Ser Leu Thr Val Ser Thr Pro Phe His Gln Glu Ala Gly Ser Ser
1425                1430                1435                1440

Thr Thr Leu Ser Ser Ile Lys Val Glu Val Ala Ser Ser Gln Ala Glu
            1445                1450                1455

Thr Thr Thr Leu Asp Gln Asp His Leu Glu Thr Thr Val Ala Ile Leu
            1460                1465                1470

Leu Ser Glu Thr Arg Pro Gln Asn His Thr Pro Thr Ala Ala Arg Met
        1475                1480                1485

Lys Glu Pro Ala Ser Ser Pro Ser Thr Ile Leu Met Ser Leu Gly
        1490                1495                1500

Gln Thr Thr Thr Lys Pro Ala Leu Pro Ser Pro Arg Ile Ser Gln
1505                1510                1515                1520

Ala Ser Arg Asp Ser Lys Glu Asn Val Phe Leu Asn Tyr Val Gly Asn
            1525                1530                1535

Pro Glu Thr Glu Ala Thr Pro Val Asn Asn Gly Thr Gln His Met
            1540                1545                1550

Ser Gly Pro Asn Glu Leu Ser Thr Pro Ser Ser Asp Arg Asp Ala Phe
1555                1560                1565

Asn Leu Ser Thr Lys Leu Glu Leu Glu Lys Gln Val Phe Gly Ser Arg
        1570                1575                1580

Ser Leu Pro Arg Gly Pro Asp Ser Gln Arg Gln Asp Gly Arg Val His
1585                1590                1595                1600

Ala Ser His Gln Leu Thr Arg Val Pro Ala Lys Pro Ile Leu Pro Thr
            1605                1610                1615

Ala Thr Val Arg Leu Pro Glu Met Ser Thr Gln Ser Ala Ser Arg Tyr
            1620                1625                1630

Phe Val Thr Ser Gln Ser Pro Arg His Trp Thr Asn Lys Pro Glu Ile
        1635                1640                1645

Thr Thr Tyr Pro Ser Gly Ala Leu Pro Glu Asn Lys Gln Phe Thr Thr
            1650                1655                1660

Pro Arg Leu Ser Ser Thr Thr Ile Pro Leu Pro Leu His Met Ser Lys
1665                1670                1675                1680

Pro Ser Ile Pro Ser Lys Phe Thr Asp Arg Arg Thr Asp Gln Phe Asn
            1685                1690                1695

Gly Tyr Ser Lys Val Phe Gly Asn Asn Asn Ile Pro Glu Ala Arg Asn
```

-continued

```
              1700                1705                1710
Pro Val Gly Lys Pro Pro Ser Pro Arg Ile Pro His Tyr Ser Asn Gly
         1715                1720                1725

Arg Leu Pro Phe Phe Thr Asn Lys Thr Leu Ser Phe Pro Gln Leu Gly
         1730                1735                1740

Val Thr Arg Arg Pro Gln Ile Pro Thr Ser Pro Ala Pro Val Met Arg
1745                1750                1755                1760

Glu Arg Lys Val Ile Pro Gly Ser Tyr Asn Arg Ile His Ser His Ser
                1765                1770                1775

Thr Phe His Leu Asp Phe Gly Pro Pro Ala Pro Pro Leu Leu His Thr
         1780                1785                1790

Pro Gln Thr Thr Gly Ser Pro Ser Thr Asn Leu Gln Asn Ile Pro Met
         1795                1800                1805

Val Ser Ser Thr Gln Ser Ser Ile Ser Phe Ile Thr Ser Ser Val Gln
         1810                1815                1820

Ser Ser Gly Ser Phe His Gln Ser Ser Lys Phe Phe Ala Gly Gly
1825                1830                1835                1840

Pro Pro Ala Ser Lys Phe Trp Ser Leu Gly Glu Lys Pro Gln Ile Leu
                1845                1850                1855

Thr Lys Ser Pro Gln Thr Val Ser Val Thr Ala Glu Thr Asp Thr Val
                1860                1865                1870

Phe Pro Cys Glu Ala Thr Gly Lys Pro Lys Pro Phe Val Thr Trp Thr
         1875                1880                1885

Lys Val Ser Thr Gly Ala Leu Met Thr Pro Asn Thr Arg Ile Gln Arg
         1890                1895                1900

Phe Glu Val Leu Lys Asn Gly Thr Leu Val Ile Arg Lys Val Gln Val
1905                1910                1915                1920

Gln Asp Arg Gly Gln Tyr Met Cys Thr Ala Ser Asn Leu His Gly Leu
                1925                1930                1935

Asp Arg Met Val Val Leu Ser Val Thr Val Gln Gln Pro Gln Ile
                1940                1945                1950

Leu Ala Ser His Tyr Gln Asp Val Thr Val Tyr Leu Gly Asp Thr Ile
         1955                1960                1965

Ala Met Glu Cys Leu Ala Lys Gly Thr Pro Ala Pro Gln Ile Ser Trp
         1970                1975                1980

Ile Phe Pro Asp Arg Arg Val Trp Gln Thr Val Ser Pro Val Glu Ser
1985                1990                1995                2000

Arg Ile Thr Leu His Glu Asn Arg Thr Leu Ser Ile Lys Glu Ala Ser
                2005                2010                2015

Phe Ser Asp Arg Gly Val Tyr Lys Cys Val Ala Ser Asn Ala Ala Gly
                2020                2025                2030

Ala Asp Ser Leu Ala Ile Arg Leu His Val Ala Ala Leu Pro Pro Val
         2035                2040                2045

Ile His Gln Glu Lys Leu Glu Asn Ile Ser Leu Pro Pro Gly Leu Ser
         2050                2055                2060

Ile His Ile His Cys Thr Ala Lys Ala Ala Pro Leu Pro Ser Val Arg
2065                2070                2075                2080

Trp Val Leu Gly Asp Gly Thr Gln Ile Arg Pro Ser Gln Phe Leu His
                2085                2090                2095

Gly Asn Leu Phe Val Phe Pro Asn Gly Thr Leu Tyr Ile Arg Asn Leu
         2100                2105                2110

Ala Pro Lys Asp Ser Gly Arg Tyr Glu Cys Val Ala Ala Asn Leu Val
         2115                2120                2125
```

-continued

```
Gly Ser Ala Arg Arg Thr Val Gln Leu Asn Val Gln Arg Ala Ala Ala
    2130                2135                2140
Asn Ala Arg Ile Thr Gly Thr Ser Pro Arg Arg Thr Asp Val Arg Tyr
2145                2150                2155                2160
Gly Gly Thr Leu Lys Leu Asp Cys Ser Ala Ser Gly Asp Pro Trp Pro
                2165                2170                2175
Arg Ile Leu Trp Arg Leu Pro Ser Lys Arg Met Ile Asp Ala Leu Phe
            2180                2185                2190
Ser Phe Asp Ser Arg Ile Lys Val Phe Ala Asn Gly Thr Leu Val Val
            2195                2200                2205
Lys Ser Val Thr Asp Lys Asp Ala Gly Asp Tyr Leu Cys Val Ala Arg
            2210                2215                2220
Asn Lys Val Gly Asp Asp Tyr Val Val Leu Lys Val Asp Val Val Met
2225                2230                2235                2240
Lys Pro Ala Lys Ile Glu His Lys Glu Glu Asn Asp His Lys Val Phe
                2245                2250                2255
Tyr Gly Gly Asp Leu Lys Val Asp Cys Val Ala Thr Gly Leu Pro Asn
                2260                2265                2270
Pro Glu Ile Ser Trp Ser Leu Pro Asp Gly Ser Leu Val Asn Ser Phe
            2275                2280                2285
Met Gln Ser Asp Ser Gly Gly Arg Thr Lys Arg Tyr Val Val Phe
            2290                2295                2300
Asn Asn Gly Thr Leu Tyr Phe Asn Glu Val Gly Met Arg Glu Glu Gly
2305                2310                2315                2320
Asp Tyr Thr Cys Phe Ala Glu Asn Gln Val Gly Lys Asp Glu Met Arg
            2325                2330                2335
Val Arg Val Lys Val Val Thr Ala Pro Ala Thr Ile Arg Asn Lys Thr
            2340                2345                2350
Tyr Leu Ala Val Gln Val Pro Tyr Gly Asp Val Thr Val Ala Cys
            2355                2360                2365
Glu Ala Lys Gly Glu Pro Met Pro Lys Val Thr Trp Leu Ser Pro Thr
            2370                2375                2380
Asn Lys Val Ile Pro Thr Ser Ser Glu Lys Tyr Gln Ile Tyr Gln Asp
2385                2390                2395                2400
Gly Thr Leu Leu Ile Gln Lys Ala Gln Arg Ser Asp Ser Gly Asn Tyr
                2405                2410                2415
Thr Cys Leu Val Arg Asn Ser Ala Gly Glu Asp Arg Lys Thr Val Trp
            2420                2425                2430
Ile His Val Asn Val Gln Pro Pro Lys Ile Asn Gly Asn Pro Asn Pro
            2435                2440                2445
Ile Thr Thr Val Arg Glu Ile Ala Ala Gly Gly Ser Arg Lys Leu Ile
        2450                2455                2460
Asp Cys Lys Ala Glu Gly Ile Pro Thr Pro Arg Val Leu Trp Ala Phe
2465                2470                2475                2480
Pro Glu Gly Val Val Leu Pro Ala Pro Tyr Tyr Gly Asn Arg Ile Thr
                2485                2490                2495
Val His Gly Asn Gly Ser Leu Asp Ile Arg Ser Leu Arg Lys Ser Asp
            2500                2505                2510
Ser Val Gln Leu Val Cys Met Ala Arg Asn Glu Gly Gly Glu Ala Arg
            2515                2520                2525
Leu Ile Val Gln Leu Thr Val Leu Glu Pro Met Glu Lys Pro Ile Phe
        2530                2535                2540
```

-continued

His Asp Pro Ile Ser Glu Lys Ile Thr Ala Met Ala Gly His Thr Ile
2545                2550                2555                2560

Ser Leu Asn Cys Ser Ala Ala Gly Thr Pro Thr Pro Ser Leu Val Trp
            2565                2570                2575

Val Leu Pro Asn Gly Thr Asp Leu Gln Ser Gly Gln Gln Leu Gln Arg
        2580                2585                2590

Phe Tyr His Lys Ala Asp Gly Met Leu His Ile Ser Gly Leu Ser Ser
    2595                2600                2605

Val Asp Ala Gly Ala Tyr Arg Cys Val Ala Arg Asn Ala Ala Gly His
    2610                2615                2620

Thr Glu Arg Leu Val Ser Leu Lys Val Gly Leu Lys Pro Glu Ala Asn
2625                2630                2635                2640

Lys Gln Tyr His Asn Leu Val Ser Ile Ile Asn Gly Glu Thr Leu Lys
                2645                2650                2655

Leu Pro Cys Thr Pro Pro Gly Ala Gly Gln Gly Arg Phe Ser Trp Thr
            2660                2665                2670

Leu Pro Asn Gly Met His Leu Glu Gly Pro Gln Thr Leu Gly Arg Val
        2675                2680                2685

Ser Leu Leu Asp Asn Gly Thr Leu Thr Val Arg Glu Ala Ser Val Phe
    2690                2695                2700

Asp Arg Gly Thr Tyr Val Cys Arg Met Glu Thr Glu Tyr Gly Pro Ser
2705                2710                2715                2720

Val Thr Ser Ile Pro Val Ile Val Ile Ala Tyr Pro Pro Arg Ile Thr
                2725                2730                2735

Ser Glu Pro Thr Pro Val Ile Tyr Thr Arg Pro Gly Asn Thr Val Lys
            2740                2745                2750

Leu Asn Cys Met Ala Met Gly Ile Pro Lys Ala Asp Ile Thr Trp Glu
        2755                2760                2765

Leu Pro Asp Lys Ser His Leu Lys Ala Gly Val Gln Ala Arg Leu Tyr
    2770                2775                2780

Gly Asn Arg Phe Leu His Pro Gln Gly Ser Leu Thr Ile Gln His Ala
2785                2790                2795                2800

Thr Gln Arg Asp Ala Gly Phe Tyr Lys Cys Met Ala Lys Asn Ile Leu
                2805                2810                2815

Gly Ser Asp Ser Lys Thr Thr Tyr Ile His Val Phe
            2820                2825

<210> SEQ ID NO 3
<211> LENGTH: 27
<212> TYPE: DNA
<213> ORGANISM: Artificial Sequence
<220> FEATURE:
<223> OTHER INFORMATION: PCR primer

<400> SEQUENCE: 3
ggagtcctgt ggcatccacg aaactac                                27

<210> SEQ ID NO 4
<211> LENGTH: 25
<212> TYPE: DNA
<213> ORGANISM: Artificial Sequence -continued

```
<220> FEATURE:
<223> OTHER INFORMATION: PCR primer

<400> SEQUENCE: 4
cacatctgct ggaaggtgga cagcg                                              25

<210> SEQ ID NO 5
<211> LENGTH: 26
<212> TYPE: DNA
<213> ORGANISM: Artificial Sequence
<220> FEATURE:
<223> OTHER INFORMATION: PCR primer

<400> SEQUENCE: 5
catgggcaca aactgactca tggctg                                             26

<210> SEQ ID NO 6
<211> LENGTH: 28
<212> TYPE: DNA
<213> ORGANISM: Artificial Sequence
<220> FEATURE:
<223> OTHER INFORMATION: PCR primer

<400> SEQUENCE: 6
gagaggagag gaaggagaaa actgcatc                                           28

<210> SEQ ID NO 7
<211> LENGTH: 37
<212> TYPE: DNA
<213> ORGANISM: Artificial Sequence
<220> FEATURE:
<223> OTHER INFORMATION: PCR primer

<400> SEQUENCE: 7
ttgcggccgc gccaccatgc ccaagcgcgc gcactgg                                 37

<210> SEQ ID NO 8
<211> LENGTH: 28
<212> TYPE: DNA
<213> ORGANISM: Artificial Sequence
<220> FEATURE:
<223> OTHER INFORMATION: PCR primer

<400> SEQUENCE: 8
tcaatactcc tgctcctgtt ctgtctca                                           28

<210> SEQ ID NO 9
<211> LENGTH: 15
<212> TYPE: PRT
<213> ORGANISM: Homo sapiens

<400> SEQUENCE: 9

Cys Met Ala Lys Asn Ile Leu Gly Ser Asp Ser Lys Thr Thr Tyr
 1               5                  10                  15
```

ARTHRITIS-ASSOCIATED PROTEIN

FIELD OF THE INVENTION

This invention relates to methods and compositions for early diagnosis, monitoring and treatment of cartilage degenerative conditions, including forms of arthritis. In particular, the invention relates to a protein differentially expressed in human subjects suffering from arthritis, such as osteoarthritis (OA) and rheumatoid arthritis (RA) compared to individuals without arthritis, antibodies that recognize this protein, and methods for diagnosing arthritis.

BACKGROUND OF THE INVENTION

Arthritis involves both cartilage breakdown and new bone formation, and in many cases, leads to the loss of joint function. While there are some insights as to the mediators contributing to cartilage remodeling, there is only limited knowledge of the underlying molecular mechanisms of arthritis. At a cellular level, the articular chondrocyte plays a key role in both to cartilage breakdown and new bone growth, and this is likely to be reflected in changes in cellular transcriptional activity. The application of genomic approaches to the understanding of the complexities of arthritis promises to yield significant advances in the diagnosis and treatment of this prevalent disease of joint degeneration.

An important priority for the investigation and clinical application of potential therapies for arthritis is the identification of biochemical markers that could be used to assess various aspects of disease activity (Chevalier, X. (1997) *Rev.Rhum. Engl. Ed.* 64: 562–577.

Lohmander, L. S. (1997) *Baillieres Clin. Rhematol.* 11: 711–726). Current research in this field is focusing on a number of possible surrogate markers of arthritis that reflect metabolic changes in the joint associated with cartilage destruction and remodeling, including hyaluronate, cartilage oligomeric matrix protein, keratan sulfate, metalloproteinase activity, and various cytokines.

To identify gene products involved in human arthritis, the present inventors have analyzed the differences in mRNA populations in diseased cartilage compared to age-matched healthy cartilage using differential display RT-PCR (Hu, S-I, Carozza, M., Klein, M., Nantermet, P., Luk, D., and Crowl, R. M. (1998) *J. Biol. Chem.* 273: 34406–34412). The inventors have discovered a large protein, termed "adlican," the presence of which in cartilage is strongly associated with arthritis, particularly osteoarthritis. An anti-peptide antibody was generated against the carboxy terminal sequence and used for immunoblot analysis to detect adlican protein in synovial fluid samples obtained from patients with arthritis.

SUMMARY OF THE INVENTION

In a first aspect, the invention provides an isolated DNA comprising a nucleotide sequence as set forth in SEQ ID NO:1. Also provided are isolated DNA's comprising nucleic acid sequences that hybridizes under high stringency conditions to the isolated DNA as set forth in SEQ ID NO:1. In a preferred embodiment, the isolated DNA takes the form of a vector molecule comprising the DNA as set forth in SEQ ID NO:1.

In a second aspect, the invention provides an isolated polypeptide with an amino acid sequence as set forth in SEQ ID NO:2. Such a polypeptide, or fragments thereof, is found in the synovial fluid of sufferers of arthritis to a much greater extent than in the synovial fluid of individuals without arthritis. In accordance with this aspect of the invention there are provided novel polypeptides of human origin as well as biologically, diagnostically or therapeutically useful fragments, variants and derivatives thereof, variants and derivatives of the,fragments, and analogs of the foregoing.

A third aspect of the present invention encompasses a method for the diagnosis of arthritis in a human which includes detecting the elevated transcription of messenger RNA transcribed from adlican-encoding DNA in cartilage from a human, where such elevated transcription is diagnostic of the human's affliction with arthritis.

Another embodiment of the assay aspect of the invention provides a method for the diagnosis of arthritis in a human which requires measuring the amount of a polypeptide that includes or is adlican or fragments of adlican in synovial fluid from a human, where the presence of an elevated amount of the polypeptide or fragments thereof, relative to the amount of the polypeptide or fragments thereof in non-arthritic synovial fluid, is diagnostic of the human's suffering from arthritis.

In accordance with one embodiment of this aspect of the invention there is provided anti-sense polynucleotides that regulate transcription of the human adlican gene.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned human adlican polypeptides comprising culturing host cells having incorporated therein an expression vector containing an exogenously-derived human adlican-encoding polynucleotide under conditions sufficient for expression of human adlican polypeptides in the host and then recovering the expressed polypeptide.

In accordance with another object the invention there are provided products, compositions, processes and methods that utilize the aforementioned polypeptides and polynucleotides for research, biological, clinical and therapeutic purposes, inter alia.

In certain additional preferred embodiments of this aspect of the invention there are provided an antibody or a fragment thereof which specifically binds to a polypeptide that comprises the amino acid sequence set forth in SEQ ID NO:2, i.e., adlican. In certain particularly preferred embodiments in this regard, the antibodies are highly selective for human adlican polypeptides or portions of human adlican polypeptides.

In a further aspect, an antibody or fragment thereof is provided that binds to a fragment or portion of the amino acid sequence set forth in SEQ ID NO:2.

In yet another aspect, the invention provides vertebrate cells which can be propagated in vitro and which are capable upon growth in culture of producing a polypeptide that comprises the amino acid sequence set forth in SEQ ID NO:2 or fragments thereof, where the cells contain transcriptional control DNA sequences, other than human adlican transcriptional control sequences, where the transcriptional control sequences control transcription of DNA encoding a polypeptide with the amino acid sequence according to SEQ ID NO:2 or fragments thereof.

In another aspect, the present invention provides a method for producing human adlican polypeptides which comprises culturing a host cell having incorporated therein an expression vector containing an exogenously-derived human adlican-encoding polynucleotide under conditions sufficient for expression of human adlican polypeptides in the host cell, thereby causing the production of an expressed polypeptide, and recovering the expressed polypeptide.

In yet another aspect of the present invention there are provided kits comprising the components necessary to detect above-normal expression of human adlican polynucleotides or polypeptides in body tissue samples derived from a patient.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 1 is a depiction of the cDNA encoding adlican (SEQ ID NO:1).

FIG. 2 is a depiction of the amino acid sequence encoded by SEQ ID NO:1 (SEQ ID NO:2).

DETAILED DESCRIPTION OF THE INVENTION

Figure 3:
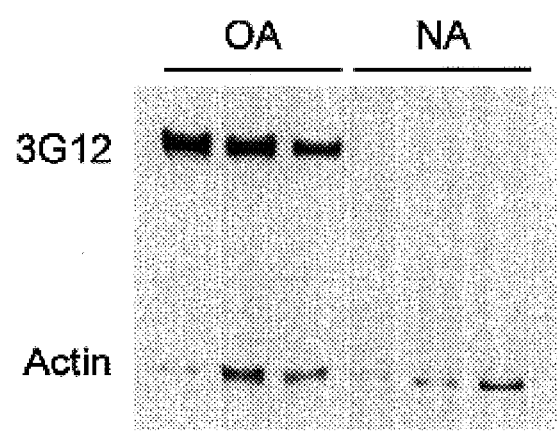
FIG. 3 is an analysis of the amount of adlican mRNA expressed in the cartilage of human osteoarthritis suffers compared with the amount of adlican mRNA expressed in the cartilage of human non-arthritic control subjects using semi-quantitative reverse transcription-PCR. Semi-quantitative reverse-transcription PCR of actin was used as a control.
Figure 4:
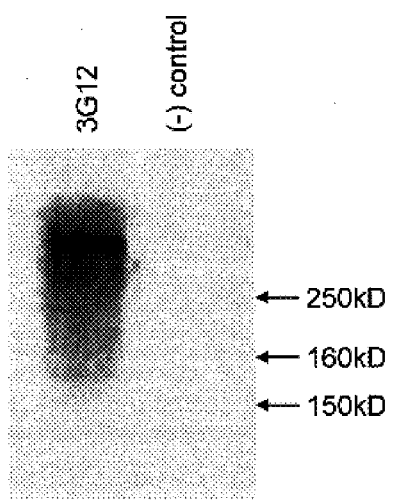
FIG. 4 is an autoradiogram of a gel showing the production of adlican in vitro using a reticulocyte lysate system.
Figure 5:
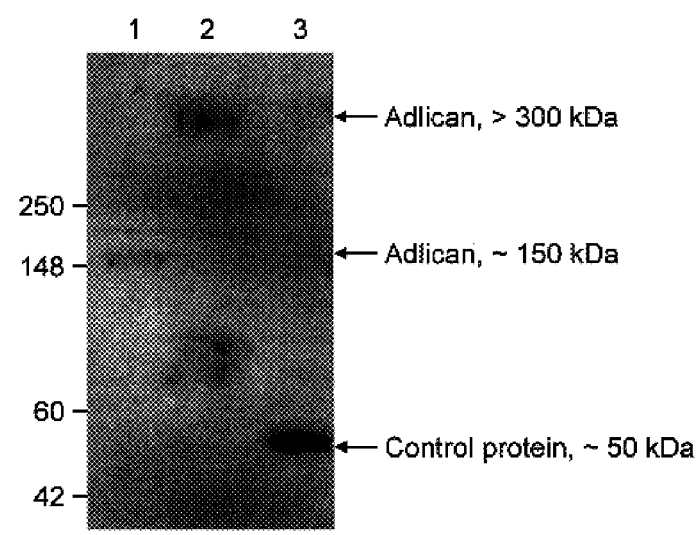
FIG. 5 is a Western Blot of a gel on which proteins from HEK 293 cells which were transfected with an adlican expression vector were run. Anti-adlican peptide antibodies were used. Lane 1 is cell extract from cells transfected with an adlican expression vector 72 hours post-infection. Lane 2 is from cells 48 hours post-infection. Lane 3 is from cells transfected with a control vector at 48 hours post-infection.

All patent applications, patents and literature references cited herein are hereby incorporated by reference in their entirety.

In practicing the present invention, many conventional techniques in molecular biology, microbiology, and recombinant DNA are used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

As used herein, "differentially expressed gene" refers to (a) a gene containing at least one of the DNA sequences disclosed herein (e.g., as shown in FIG. 1 and SEQ ID NO:1); (b) any DNA sequence that encodes the amino acid sequence encoded by the DNA sequences disclosed herein (e.g., as shown in FIG. 2 and SEQ ID NO:2); or (c) any DNA sequence that is substantially similar to the coding sequences disclosed herein.

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 80%, more desirably at least 85%, preferably at least 90%, more preferably at least 95%, still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0, or at http://www-hto.usc.edu/software/seqaln/index.html). The localS program, version 1.16, is used with following parameters: match: 1, mismatch penalty: 0.33, open-gap penalty: 2, extended-gap penalty: 2. A nucleotide sequence "substantially similar" to reference nucleotide sequence hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C., yet still encodes a functionally equivalent gene product.

The differentially expressed genes disclosed herein are expressed in arthritic tissues (e.g., cartilage in a human afflicted with arthritis) in elevated amounts relative to, i.e., to a greater extent than in the corresponding tissues of humans who do not suffer from arthritis. Messenger RNA transcribed from the differentially expressed genes, and protein translated from such mRNA, is present in arthritic tissues and/or synovial fluid associated with such tissues in an amount at least about twice, preferably at least about five times, more preferably at least amount ten times, most preferably at least about 100 times the levels of mRNA and protein found in corresponding tissues found in humans who do not suffer from arthritis. Such elevated transcription of adlican mRNA is referred to herein as "elevated transcription."

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and the like.

"Heterologous" as used herein means "of different natural origin" or represent a non-natural state. For example, if a host cell is transformed with a DNA or gene derived from another organism, particularly from another species, that gene is heterologous with respect to that host cell and also with respect to descendants of the host cell which carry that gene. Similarly, heterologous refers to a nucleotide sequence derived from and inserted into the same natural, original cell type, but which is present in a non-natural state, e.g. a different copy number, or under the control of different regulatory elements.

A vector molecule is a DNA molecule into which heterologous DNA may be inserted which can then replicate in an appropriate host cell. Vectors must have one or more origin of replication, and one or more site into which the recombinant DNA can be inserted. Vectors often have convenient means by which cells with vectors can be selected from those without, e.g., they encode drug resistance genes. Common vectors include plasmids, viral genomes, and (primarily in yeast) "artificial chromosomes."

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

As used herein, the term "transcriptional control sequence" refers to DNA sequences, such as initiator sequences, enhancer sequences, and promoter sequences, which induce, repress, or otherwise control the transcription of protein encoding nucleic acid sequences to which they are operably linked.

As used herein, "human adlican transcriptional control sequences" are any of those transcriptional control sequences normally found associated with the human adlican gene in as it is found in the human X chromosome.

As used herein, "non-human transcriptional control sequence" is any transcriptional control sequence not found in the human genome.

The term "polypeptide" is used interchangeably herein with the terms "polypeptides" and "protein(s)".

The invention also includes nucleic acid molecules, preferably DNA molecules, that hybridize to, and are therefore the complements of, the DNA sequences (a) through (c), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6.times.SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may act as target gene antisense molecules, useful, for example, in target gene regulation and/or as antisense primers in amplification reactions of target gene nucleic acid sequences. Further, such sequences may be used as part of ribozyme and/or triple helix sequences, also useful for target gene regulation. Still further, such molecules may be used as components of diagnostic methods whereby the presence of a cardiovascular disease-causing allele, may be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression.

The invention includes fragments of any of the DNA sequences disclosed herein. Fragments of the full length adlican gene may be used as a hybridization probe for a cDNA library to isolate the full length gene and to isolate other genes which have a high sequence similarity to the adlican gene or similar biological activity. Probes of this type preferably have at least about 30 bases and may contain, for example, from about 30 to about 50 bases, about 50 to about 100 bases, about 100 to about 200 bases, or more than 200 bases. The probe may also be used to identify a cDNA clone corresponding to a full length transcript and a genomic clone or clones that contain the complete ADLICAN gene including regulatory and promotor regions, exons, and introns. An example of a screen comprises isolating the coding region of the ADLICAN gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

In addition to the gene sequences described above, homologs of such sequences, as may, for example be present in other species, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, the isolated differentially expressed gene sequence may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Further, a previously unknown differentially expressed gene-type sequence may be isolated by performing PCR using two degenerate oligonucleotide primer pools designed on the basis of amino acid sequences within the gene of interest. The template for the reaction may be cDNA obtained by reverse transcription of mRNA prepared from human or non-human cell lines or tissue known or suspected to express a differentially expressed gene allele.

The PCR product may be subcloned and sequenced to ensure that the amplified sequences represent the sequences of a differentially expressed gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard procedures, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the differentially expressed gene identified is the normal, or wild type, gene, this gene may be used to isolate mutant alleles of the gene. Such an isolation is preferable in processes and disorders which are known or suspected to have a genetic basis. Mutant alleles may be isolated from individuals either known or suspected to have a genotype which contributes to cardiovascular disease symptoms. Mutant alleles and mutant allele products may then be utilized in the diagnostic assay systems described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof may then be labeled and used as a probed to identify the corresponding mutant allele in the library. The clone containing this gene may then be purified through methods routinely practiced in the art, and subjected to sequence analysis as described above.

Additionally, an expression library cart be constructed utilizing DNA isolated from or cDNA synthesized from a tissue known to or suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described above.

Differentially expressed gene products include those proteins encoded by nucleotide sequence set forth in SEQ ID NO:1, in particular, a polypeptide that is or includes the amino acid sequence set out in SEQ ID NO:2, or fragments thereof.

In addition, differentially expressed gene products may include proteins that represent functionally equivalent gene products. Such an equivalent differentially expressed gene product may contain deletions, additions or substitutions of amino acid residues within the amino acid sequence encoded by the differentially expressed gene sequences described, above, but which result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous differentially expressed gene products encoded by the differentially expressed gene sequences described above. Alternatively, when utilized as part of assays such as those described, below, "functionally equivalent" may refer to peptides capable of interacting with other cellular or extracellular molecules in a manner substantially similar to the way in which the corresponding portion of the endogenous differentially expressed gene product would.

The differentially expressed gene products may be produced by recombinant DNA technology using techniques well known in the art. Thus, methods for preparing the differentially expressed gene polypeptides and peptides of the invention by expressing nucleic acid encoding differentially expressed gene sequences are described herein. Methods which are well known to those skilled in the art can be used to construct expression vectors containing differentially expressed gene protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding differentially expressed gene protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the differentially expressed gene coding sequences of the invention. Such host-expression systems represent vehicles by which the coding sequences of interest may be produced and subsequently purified, but also represent cells which may, when transformed or transfected with the appropriate nucleotide coding sequences, exhibit the differentially expressed gene protein of the invention in situ. These include but are not limited to microorganisms such as bacteria (e.g., E. coli, B. subtilis) transformed with recombinant bacteriophage DNA, plasmid DNA or cosmid DNA expression vectors containing differentially expressed gene protein coding sequences; yeast (e.g. Saccharomyces, Pichia) transformed with recombinant yeast expression vectors containing the differentially expressed gene protein coding sequences; insect cell systems infected with recombinant virus expression vectors (e.g., baculovirus) containing the differentially expressed gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing differentially expressed gene protein coding sequences; or mammalian cell systems (e.g. COS, CHO, BHK, 293, 3T3) harboring recombinant expression constructs containing promoters derived from the genome of mammalian cells (e.g., metallothioneine promoter) or from mammalian viruses (e.g., the adenovirus late promoter; the vaccinia virus 7.5K promoter).

Expression of adlican by a cell from an adlican gene that is native to a the cell can also be performed. Methods for such expression are detailed in, e.g., U.S. Pat. Nos. 5,641,670; 5,733,761; 5,968,502; and 5,994,127, all of which are expressly incorporated by reference herein in their entirety.

In bacterial systems, a number of expression vectors may be advantageously selected depending upon the use intended for the differentially expressed gene protein being expressed. For example, when a large quantity of such a protein is to be produced, for the generation of antibodies or to screen peptide libraries, for example, vectors which direct the expression of high levels of fusion protein products that are readily purified may be desirable. Such vectors include, but are not limited to, the E. coli expression vector pUR278 (Ruther et al., 1983, EMBO J. 2:1791), in which the differentially expressed gene-protein coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene protein can be released from the GST moiety.

Promoter regions can be selected from any desired gene using vectors that contain a reporter transcription unit lacking a promoter region, such as a chloramphenicol acetyl transferase ("cat") transcription unit, downstream of restriction site or sites for introducing a candidate promoter fragment; i.e., a fragment that may contain a promoter. As is well known, introduction into the vector of a promoter-containing fragment at the restriction site upstream of the cat gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well known and readily available promoters, but also promoters that readily may be obtained by the foregoing technique, using a reporter gene.

Among known bacterial promoters suitable for expression of polynucleotides and polypeptides in accordance with the present invention are the E. coli lacI and lacZ promoters, the T3 and T7 promoters, the T5 tac promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

In an insect system, Autographa californica nuclear polyhedrosis virus (AcNPV) is one of several insect systems that can be used as a vector to express foreign genes. The virus grows in Spodoptera frugiperda cells. The differentially expressed gene coding sequence may be cloned individually into non-essential regions (for example the polyhedrin gene) of the virus and placed under control of an AcNPV promoter (for example the polyhedrin promoter). Successful insertion of differentially expressed gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the differentially expressed gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing differentially expressed gene protein in infected hosts. (E.g., See Logan & Shenk, 1984, Proc. Natl. Acad. Sci. USA 81:3655–3659). Specific initiation signals may also be required for efficient translation of inserted differentially expressed gene coding sequences. These signals include the ATG initiation codon and adjacent sequences. In cases where an entire differentially expressed gene, including its own initiation codon and adjacent sequences, is inserted into the appropriate expression vector, no additional translational control signals may be needed. However, in cases where only a portion of the differentially expressed gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

Selection of appropriate vectors and promoters for expression in a host cell is a well known procedure and the requisite techniques for expression vector construction, introduction of the vector into the host and expression in the host per se are routine skills in the art.

Generally, recombinant expression vectors will include origins of replication, a promoter derived from a highly-expressed gene to direct transcription of a downstream structural sequence, and a selectable marker to permit isolation of vector containing cells after exposure to the vector.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, W138, etc.

For long-term, high-yield production of recombinant proteins, stable expression is preferred. For example, cell lines which stably express the differentially expressed gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the differentially expressed gene protein. Such engineered cell lines may be particularly useful in screening and evaluation of compounds that affect the endogenous activity of the differentially expressed gene protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

An alternative fusion protein system allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

When used as a component in assay systems such as those described below, the differentially expressed gene protein may be labeled, either directly or indirectly, to facilitate detection of a complex formed between the differentially expressed gene protein and a test substance. Any of a variety of suitable labeling systems may be used including but not limited to radioisotopes such as $^{125}I$; enzyme labeling systems that generate a detectable calorimetric signal or light when exposed to substrate; and fluorescent labels.

Where recombinant DNA technology is used to produce the differentially expressed gene protein for such assay systems, it may be advantageous to engineer fusion proteins that can facilitate labeling, immobilization and/or detection.

Indirect labeling involves the use of a protein, such as a labeled antibody, which specifically binds to either a differentially expressed gene product. Such antibodies include but are not limited to polyclonal, monoclonal, chimeric, single chain, Fab fragments and fragments produced by an Fab expression library.

Described herein are methods for the production of antibodies capable of specifically recognizing one or more differentially expressed gene epitopes. Such antibodies may include, but are not limited to polyclonal antibodies, monoclonal antibodies (mAbs), humanized or chimeric antibodies, single chain antibodies, Fab fragments, F(ab')₂ fragments, fragments produced by a Fab expression library, anti-idiotypic (anti-Id) antibodies, and epitope-binding fragments of any of the above. Such antibodies may be used, for example, in the detection of a fingerprint, target, gene in a biological sample, or, alternatively, as a method for the inhibition of abnormal target gene activity. Thus, such antibodies may be utilized as part of cardiovascular disease treatment methods, and/or may be used as part of diagnostic techniques whereby patients may be tested for abnormal levels of adlican, or for the presence of abnormal forms of adlican.

For the production of antibodies to a differentially expressed gene, various host animals may be immunized by injection with a differentially expressed gene protein, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with differentially expressed gene product supplemented with adjuvants as also described above.

Monoclonal antibodies, which are homogeneous populations of antibodies to a particular antigen, may be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce differentially expressed gene-single chain antibodies. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

Particularly preferred, for ease of detection, is the sandwich assay, of which a number of variations exist, all of which are intended to be encompassed by the present invention.

For example, in a typical forward assay, unlabeled antibody is immobilized on a solid substrate and the sample to be tested brought into contact with the bound molecule. After a suitable period of incubation, for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an adlican-specific antibody.

The most commonly used reporter molecules in this type of assay are either enzymes, fluorophore- or radionuclide-containing molecules. In the case of an enzyme immunoassay an enzyme is conjugated to the second antibody, usually by means of glutaraldehyde or periodate. As will be readily recognized, however, a wide variety of different ligation techniques exist, which ae well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. A solution containing the appropriate substrate is then added to the tertiary complex of antibody-adlican-labeled antibody. The substrate reacts with the enzyme linked to the second antibody, giving a qualitative visual signal, which may be further quantitated, usually spectrophotometrically, to give an evaluation of the amount of adlican which is present in the serum sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

The present invention also includes a kit for performing the assay aspect of the invention. Such a kit includes vials or vessels for incubating a body tissue or fluid sample, and the components necessary for quantifying human adlican polynucleotides, for example, via RT-PCR. A kit for quantifying human adlican polypeptide may contain anti-adlican antibodies, for example, the antibodies may be prepared via the procedure set forth in Example 5.

The following Examples illustrate the present invention, without in any way limiting the scope thereof.

EXAMPLES

Example 1

Cloning of Adlican

Differential display RT-PCR is used to identify gene products with altered expression in diseased cartilage from humans suffering from OA compared to cartilage from non-arthritic (NA) human controls. As described by Hu et al., above, first strand cDNA is synthesized from 0.2 µg of total RNA with each of the 3 anchored oligo-dT primers from GenHunter Corporation, Nashville, Tenn. The reaction (20 µl) was carried out at 37° C. for 60 min. For PCR amplification, 1 µl of the cDNA serves as template in a 10 µl reaction mix containing 10 mM Tris-HCl (pH 8.4), 1.5 mM $MgCl_2$, 50 mM KCl, 0.001% gelatin, 2 µM dNTPs, 0.2 µM of 5' arbitrary primer (AP-3 from the RNAimage kit obtained from GenHunter Corporation, Nashville, Tenn.), 2 µM of the same anchored primer used in the cDNA synthesis, 5 µCi of $\alpha$-[$^{33}$P]dATP (2,000 Ci/mmole, Dupont-New England Nuclear, Boston, Mass.) and 2.5 units of AmpliTaq DNA polymerase (Perkin-Elmer, Norwalk, Conn.). Samples are subjected to 40 cycles of amplification under the following conditions: denaturing at 94° C., 30 sec, annealing at 40° C., 2 min, extension at 72° C., 30 sec, and a final extension at 72° C., 5 min. The resulting PCR products are resolved on a denaturing polyacrylamide gel and visualized by autoradiography of the dried gel. PCR products of interest are excised from the gel, and the DNA is eluted and re-amplified by PCR using the same primers and conditions described above, excluding the radio-labeled nucleotide. PCR products are analyzed on a 1.5% agarose gel and are ligated into the cloning vector PCR II 2.1 (TA cloning Kit, Invitrogen, Carlsbad, Calif.). Clones of the PCR-generated fragments are obtained by transformation of *E. Coli* strain DH5α (Gibco/BRL, Gaithersberg, Md.). DNA sequences are determined for at least 3 independent clones of each fragment using Dye Terminator Cycle Sequencing on an ABI PRISM 377 DNA sequencing system (Perkin-Elmer, Norwalk, Conn.).

As described by Hu et al, above, first strand cDNA is synthesized from total RNA isolated from OA and non-arthritic cartilage. 200 ng of total RNA and 10 pmoles of primer $T_{30}VN$ (where V=A,C,G and N=A,C,G,T) are mixed in a 6 µl volume, heated to 72° C. for 3 min and quenched on ice for 3 minutes Buffer and MMLV reverse transcriptase are added to final concentrations of 50 mM Tris-HCl (pH 8.3), 6 mM $MgCl_2$, 75 mM KCl, 1 mM dNTPs, and 10 units MMLV reverse transcriptase in 10 µl. This mixture is incubated at 42° C. for 1.5 hr, 94° C. for 5 min, and quenched on ice. Serial dilutions of cDNA from different individuals are used for PCR amplification with a primer set for actin (forward:

GGAGTCCTGTGGCATCCACGAAACTAC (SEQ ID NO:3), and reverse:

CACATCTGCTGGAAGGTGGACAGCG (SEQ ID NO:4) and for 3G12 (forward:

CATGGGCACAAACTGACTCATGGCTG (SEQ ID NO:5) and reverse:

GAGAGGAGAGGAAGGAGAAAACTGCATC (SEQ ID NO:6)) under the following conditions: 25 µl reaction volume with 10 mM Tris-HCl (pH 8.3), 50 m,M KCl, 1.5 mM $MgCl_2$, 0.001% gelatin, 20 µM of dNTPS, 1.25 units AmpliTaq Gold Polymerase (Perkin Elmer, Norwalk, Conn.); 94° C., 8.5 minutes; 32 cycles of 94° C., 30 seconds; 63° C., 30 seconds; 72° C., 2 minutes, and a final incubation at 72° C., 7 minutes. Nine µl of the reaction mix is run on a 10% polyacrylamide gel, stained with SYBR™ Green I (Molecular Probes, Eugene, OR), and quantified using fluorescence imaging and ImageQuant software (Molecular Dynamics, Sunnyvale, Calif.). The resulting PCR fragment for 3G12 is 155 bp. Concentrations are chosen to ensure that the reaction is within the log phase of amplification. Levels of expression are normalized to the levels of actin for each sample. A negative control reaction with no template is carried out for each primer set to verify the absence of contamination.

From this screening approach, several differentially expressed transcripts are obtained, including a 251 bp clone designated 3G12 (detected with 5' primer AP-3 and 3' primer oligo dT with G, $12^{th}$ clone isolated). The sequence of 3G12 is determined to be a novel sequence identified in the screen. Using PCR primers designed based on the 3G12 sequence, the corresponding transcript is found to be expressed over 100 times greater in OA cartilage than in NA cartilage by semi-quantitative RT-PCR (FIG. 3). Because of the high degree of differential expression, 3G12 is pursued as a diagnostic marker gene for OA.

The cloned 251 bp PCR-generated 3G12 fragment is used as a probe to identify a λgt11 phage clone designated "106A" with a 1.4 kb insert in a human placenta cDNA library. From a human placental 5'-STRETCH PLUS cDNA Library (Oligo dT+ random primed, Clontech, Palo Alto, Calif.), $10^7$ pfu were divided into 40 sub-libraries and screened by PCR using 3G12-specific primers. Positive fractions were further divided into 21 second-round sub-libraries which were also screened by PCR. Phage from the positive second-round sub-libraries were plated on *E. coli* strain Y 1090 and screened by plaque hybridisation using a PCR-generated probe (251 bp) labeled with [$^{32}$p] dATP. Filters were hybridized at 38° C. for 2.5 hours and washed at 48° C. three times in 1×SSC containing 0.1%. SDS. Positive plaques were identified by autoradiography, isolated and amplified, and re-screened until positive single phage clones were confirmed.

A BLASTX analysis of the sequence of 106A identifies a partial open reading frame (ORF) with coding sequence related to the L1 neural cell adhesion molecule (Coutelle, O., Nyakatura, G., Taudien, S., Elgar, G., Brehner, S., Platzer, M., Drescher, B., Jouet, M., Kenwrick, S., and Rosenthal, A. (1998) *Gene* 208: 7–15), neurofascin (Hassel, B., Rathjen, F. G., and Volkmer, H. (1997) *J Biol Chem* 272: 28742–28749), and to perlecan, a large heparan sulfate containing proteoglycan (Murdoch, A. D., Dodge, G. R., Cohen, I., Tuan, R. S., Iozzo, R. V. (1992) *J Biol Chem* 267: 8544–8557). Although it is evident that 106A represents a partial transcript, no cDNA clones are yet identified with additional upstream sequences. A repeated search of the Genbank and the EST sequence databases is conducted, and a small number of EST sequences corresponding to 3G12 are found. However, none of these sequences include the 5'-segment of cDNA clone 106A.

Clone 106A is used to identify a human genomic clorie (Genome Systems, St. Louis, Mo., P1 clone #14414). Subclones of the P1 isolate are obtained, are characterized by DNA sequence analysis, and are found to contain 2 complete and 1 incomplete exons. The 5'-most exon region is then used as a probe to identify another cDNA clone from the placental library, designated N3. The sequence of N3 extends the ORF, revealing additional homologies to NCAM and perlecan; however, the sequence lacks any evident translational initiation site.

An approach known as 5' RACE (rapid amplification of cDNA ends) is then used to obtain extended clones. Separate first strand cDNA syntheses are carried out with 500 ng of total RNA isolated and pooled from 4 OA cartilage samples. Aliquots are combined for the synthesis of double stranded cDNA with anchors ligated at both ends according to the Marathon™ cDNA system (Clontech, Palo Alto, Calif.). The antisense primer is derived from the sequence of cDNA clone N3. Utilization of the 5' RACE method yields an additional ~500 bp of coding sequence, although still with no evident translational start site. The 5'-most sequence from the RACE clones is used to isolate a second genomic clone, and its sub-clone E3. A search of Genbank reveals that the sequence of E3 is 100% identical to a 3 kb segment of a sequence deposited into Genbank (Accession number AC004616,), human genomic clone BAC536K7 (149,752 bp) containing a segment of the X chromosome.

The sequence of BAC536K7 is extensively analysed for predicted exons encoding the transcript corresponding to clone 3G12. Various exon prediction programs (e.g. GENESCAN, GRAIL) are used to find the rest of the gene encoding 3G12. PCR experiments are required to test for the presence of putative exons using the original placental cDNA library as template. The 5' exon (X1, exons are referred to 5' to 3' in their order in the gene, X1, X2, etc.) predicted by GENESCAN to contain the translation start site is found to be incorrect. Only by visual inspection using ORF FINDER of small potential coding exons, which contain apparent secretory signal sequences connected to sequences homologous to proteins in common with a down stream exon is the correct 5' exon identified. Exons X1, X2, X3, and X4 are verified by PCR using human placental cDNA as template and primers which bridged pairs of exons. The complete sequence of the 3G12 transcript is derived from 6 exons (X5 and X6 represented by clones N3 and 106A). The entire DNA sequence and encoded protein sequence are shown in FIGS. 1 and 2, respectively. The large adlican protein (2,828 amino acids) contains five leucine-rich repeats in the amino terminal region downstream of the signal sequence, distinct regions of homology to neural cell adhesion molecule and perlecan containing immunoglobulin C2 domains, and a mucin-like domain. Based on its predicted functionalities, the protein is termed "adlican"—for ADhesion protein with Leucine-rich repeats and Immunoglobulin domains related to perleCAN.

Example 2

Assembly of Expression Construct for Adlican

In order to produce adlican protein and examine its biochemical properties, multiple sub-cloning steps are required to assemble the various cDNA and genomic clone fragments, comprising the entire coding region, into an expression vector. A first construct is made as follows. A λgt11 clone which contains 347 bp of 5' UTR and 1–715 bp of coding region is used as a template for PCR. The PCR primer sequences used were:

Upstream (contains a NotI site and the initiation codon ATG)
5'- TTGCGGCCGCGCCACCATGCCCAAGCGCGCG CACTGG-3' (SEQ ID NO:7); and Downstream
5'-TCAATACTCCTGCTCCTGTTCTGTCTCA-3' (SEQ ID NO:8).

During the PCR reaction a NotI site is added at the 5'-end to enable subcloning into an expression vector and the 3'-end contained an EcoRI site which is present in the original adlican sequence. The 715bp NotI-EcoRI fragment is subcloned into the pcDNA 3 vector (Invitrogen, Carlsbad, Calif.) and the nucleotide sequence is verified using an Applied Biosystems 373 automated DNA sequencer and dideoxy terminator chemistry. This fragment also contains a signal sequence of 19 amino acids.

The following cDNA clones are used to generate a second construct. Clone E3 which contains coding regions from 1513–5482 bp is cut with HindIII and EcoRI and a 3969 bp fragment which corresponds to base pairs 1513–5162 of adlican is subcloned into the pcDNA3 vector. A HindIII-HindIII fragment which contains sequences corresponding to base pairs 734–1512 bp (778 bp) of adlican is generated by PCR using the D5 clone as a template, subdloned and sequenced. The vector that contains the 3969 base pair EcoRI-HindIII fragment is cut with HindIII and the 778 bp HindIII-HindIII fragment is ligated into it. The clone containing the HindIII fragment in the correct orientation contains cDNA sequence corresponding to base pairs 734–5162 of the original sequence. A 19 base pair EcoRI-HindIII adaptor which contains sequence corresponding to base pairs 716–733 is synthesized and ligated to construct II which is partially digested with HindIII to open up the 5' HindIII site located at bp734. This completes construction of the second construct, which contains an insert of 4446 lbp (base pairs 716–5162) of the original sequence.

The third construct is generated from E3 and two other cDNA clones N3 and 106A. E3 is cut with EcoRI-HindIII to generate a 320 bp fragment corresponding to base pairs 5163–5482 of adlican. N3 is cut with HindIII-ApaLI to generate a 297 bp fragment corresponding to base pairs 5483–5780 of adlican. Clone 106A is cut with ApaLI-XhoI to generate a 2707 bp fragment which corresponds to base pairs 5780–8487 of adlican. This fragment also contains a stop codon at base pair 8484. The EcoRI-HindIII, HindIII-ApaLI and ApaLI-XhoI fragments are put together by a trimolecular ligation and are subcloned into EcoRI-XhoI cut pcDNA3 to generate a 3325 bp fragment, i.e., the third construct, corresponding to base pairs 5162–8487 of adlican.

In order to generate the full length clone, the third construct is cut with EcoRI and NotI and the NotI-EcoRI insert of the first construct from above is ligated into it to generate a fourth construct of 4040 bp. The second construct from above is cut with EcoRI and the 4446 bp insert is gel purified.

The fourth construct is digested with EcoRI and the 4446 bp EcoRI insert of the second construct is ligated into it to generate the final full length fifth construct. Clones which have the EcoRI fragment of the second construct in the right orientation represent the full length clone for adlican. The stop codon is removed from the full length insert and further subcloned in frame into a hexa-histidine tag containing vector (Invitrogen, Carlsbad, Calif.) for in vitro and in vivo expression.

Example 3

Expression of the Full-length Construct in a TNT; Reticulocyte Lysate Coupled Transcription/ Translation System The plasmid DNA containing the full length insert is translated in a TNT® coupled reticulocyte lysate system (Promega, Madison, Wis.) as described by the manufacturer. The reaction mixture containing TNT® rabbit reticulocyte lysate, TNT® reaction buffer, T7 RNA polymerase, amino acid mixture minus methionine, [$^{35}$S]-methionine (>1000 Ci/mmole) Rnasin-ribonuclease inhibitor, 0.5 µg of pcDNA 3.1 (Invitrogen, Carlsbad, Calif.), DNA containing the full length adlican insert and transcend biotin-lysyl-tRNA is incubated at 30° C. for 60–90 minutes. At the end of the incubation an aliquot of the reaction is denatured in SDS containing sample buffer and electrophoresed on a 4–20% gradient polyacrylamide gel. The gel is dried after soaking for 5 minutes in 7% acetic acid, 7% methanol, 1% glycerol containing buffer and translated products are visualized by autoradiography.

Example 4

Transient Expression of the Full-length Construct in HEK 293 Cells

HEK 293 cells are seeded (200,000/well) into 6 well plates in DMEM medium containing 10% FBS and are incubated at 37° C. for 48–72 hours until the cells are about 70% confluent. The cells are transfected with the full length adlican construct in the pcDNA 3.1 vector using lipofectamine/Plus reagent (Gibco/BRL, Gaithersberg, Md.). The DNA is precomplexed with the Plus reagent for 15 minutes and then is incubated with diluted lipofectamine reagent for a further 15 minutes. The cells are washed and transferred to serum-free medium and the DNA/lipofectamine mixture is added and incubated for 3 hours at 37° C. The transfection medium is removed and is replaced with complete medium (DMEM containing 10% FBS). The cells are incubated overnight. The cells are shifted into DMEM containing 0.2% FBS the next day and are incubated for a further 48 hours. Aliquots of the supernatant are collected 48 hours and 72 hours post-transfection, are denatured and are electrophoresed on a 4–20% gradient polyacrylamide gel. The proteins in the gel were electroblotted on to a PVDF membrane (BioRad, Hercules, Calif.) and probed with anti hexa-his antibody (Qiagen, Valencia, Calif.). The bound antibody was visualized using the ECL reagent system (Amersham, Piscataway, N.J.).

Example 5

Generation of Antibodies That Recognize and Bind to Adlican

An anti-peptide antibody is generated against a sequence near the carboxy-terminus of adlican based on the predicted coding sequence of the first cDNA clone, 106A. A 15 residue peptide (CMAKNILGSDSKTTY (SEQ ID NO:9)), corresponding to the sequence of the adlican protein near the carboxyl terminus, is designed based on surface probability as determined using the program PROTEAN, a component of the LASERGENE suite of programs (DNASTAR Inc., Madison, Wis.). The peptide is synthesized, purified, and used to immunize two rabbits following a standard protocol (Genosys Biotechnologies, The Woodlands, Tex.). Antiserum from one of the immunized animals which shows the highest titer against the peptide is used for immunoblot analysis. Samples (4 µl) of human synovial fluid are subjected to SDS polyacrylamide gel electrophoresis, are transferred to PVDF membranes (BioRad, Hercules, Calif.), are analyzed for immunoreactivity using a 1:500 dilution of the antiserum, using the ECL detection system (chemiluminescent) (Amersham, Piscataway, N.J.).

Figure 6:
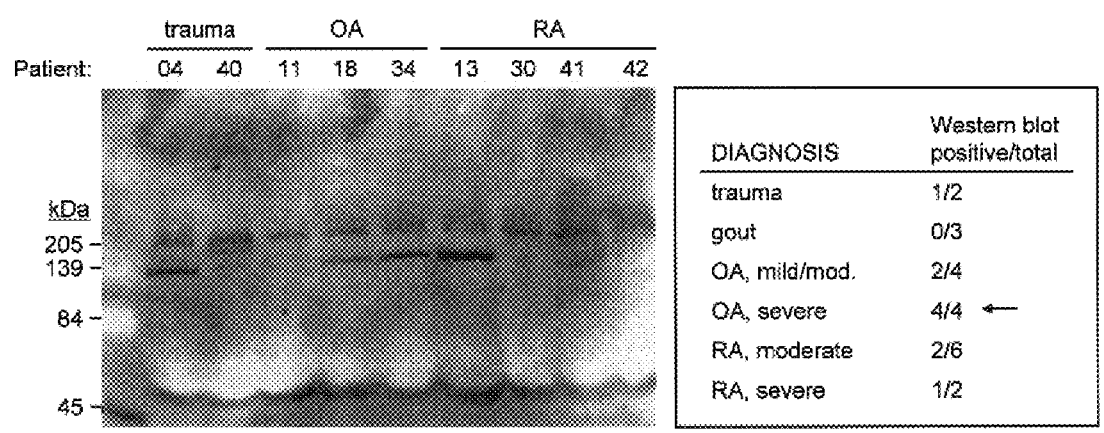
FIG. 6 is a Western Blot of a gel on which synovial fluid samples from humans suffering from trauma, osteoarthritis, and rheumatoid arthritis were tested. Anti-adlican peptide antibodies were used.

The resulting antiserum is used for detecting adlican protein in human synovial fluid by immunoblot analysis. The data in FIG. 6 include an example of one of the immunoblots where adlican protein fragment is detected in human synovial fluid and a tabulation of results derived from several blots where synovial fluids from individual patients with varied diagnoses are tested. The diagnoses are osteoarthritis, rheumatoid arthritis, gout, and joint trauma. 100% of the patients with severe OA show a positive adlican protein immunoreactivity.

What is claimed is:

1. An isolated DNA comprising a nucleotide sequence as set forth in SEQ ID NO:1.

2. A host cell comprising the isolated DNA according to claim 1.

3. An isolated DNA comprising a nucleic acid sequence that encodes the polypeptide with the amino acid sequence set forth in SEQ ID NO:2.

4. A vector molecule comprising an isolated DNA according to claim 3.

5. A vector molecule according to claim 4 comprising transcriptional control sequences.

6. A host cell comprising a vector molecule according to claim 4.

7. A vertebrate host cell which can be propagated in vitro and which is capable upon growth in culture of producing a polypeptide with the amino acid sequence set forth in SEQ ID NO:2, wherein said cell comprises at least one transcriptional control sequence that is not a human adlican transcriptional control sequence, wherein said one or more transcriptional control sequences control transcription of DNA encoding a polypeptide with the amino acid sequence set forth in SEQ ID NO:2.

8. A vertebrate cell according to claim 7 wherein said one or more transcriptional control DNA sequences are non-human transcriptional control sequences.

9. A method for producing a polypeptide which comprises:

culturing a host cell having incorporated therein an expression vector containing an exogenously-derived DNA of claim 3 under conditions sufficient for expression of a polypeptide encoded by the DNA of claim 3 in the host cell, thereby causing the production of an expressed polypeptide; and recovering the polypeptide produced by said cell.

10. An isolated DNA molecule with a nucleotide sequence complementary to the nucleotide sequence of the isolated DNA according to claim 1.

* * * * *